(12) United States Patent
Morgan

(10) Patent No.: US 8,361,774 B2
(45) Date of Patent: Jan. 29, 2013

(54) RECOMBINANT TYPE II RESTRICTION ENDONUCLEASE, NMEAIII, AND A PROCESS FOR PRODUCING THE SAME

(75) Inventor: Richard D. Morgan, Middleton, MA (US)

(73) Assignee: New England Biolabs, Inc., Ipswich, MA (US)

( * ) Notice: Subject to any disclaimer, the term of this patent is extended or adjusted under 35 U.S.C. 154(b) by 96 days.

(21) Appl. No.: 12/518,339

(22) PCT Filed: Dec. 21, 2007

(86) PCT No.: PCT/US2007/088522
§ 371 (c)(1),
(2), (4) Date: Jun. 9, 2009

(87) PCT Pub. No.: WO2008/083065
PCT Pub. Date: Jul. 10, 2008

(65) Prior Publication Data
US 2010/0159534 A1    Jun. 24, 2010

Related U.S. Application Data

(60) Provisional application No. 60/877,265, filed on Dec. 27, 2006.

(51) Int. Cl.
*C12Q 1/44* (2006.01)
*C12Q 1/68* (2006.01)
*C12N 9/22* (2006.01)
*C12N 9/16* (2006.01)
*C07K 14/00* (2006.01)
*C12P 21/00* (2006.01)

(52) U.S. Cl. ......... 435/199; 435/196; 435/69.1; 435/19; 435/6.1; 530/350

(58) Field of Classification Search ................. 435/196, 435/199, 69.1; 530/350
See application file for complete search history.

(56) References Cited

U.S. PATENT DOCUMENTS 7,115,407 B2   10/2006 Morgan et al.
2004/0091911 A1*   5/2004 Morgan et al. .............. 435/6

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Guo et al., PNAS 101(25):9205-9210, 2004.*
Roberts and Macelis, Nucl. Acids Res. 29:268-269 (2001).
Roberts et al. Nucl. Acids Res. 31:1805-1812 (2003).
Ng et al. Nucleic Acids Res. 34(12):e84 (2006).
Dempsey et al., J. Bacteriol. 188(16): 5904-5914 (2006).

* cited by examiner

*Primary Examiner* — Delia Ramirez
(74) *Attorney, Agent, or Firm* — New England Biolabs, Inc.; Harriet M. Strimpel

(57) ABSTRACT

A protein is described that has an amino acid sequence characterized by at least 90% sequence identity with SEQ ID NO: 24, the protein being capable of recognizing a sequence consisting of 5'-GCCGAG-3' within the double-stranded DNA and cleaving the substrate predominantly at 21/19 nucleotides from the recognition site. A method is also described that utilizes the protein for creating a DNA tag for use as a unique identifier for paired end sequencing of DNA or serial analysis of gene expression.

5 Claims, 18 Drawing Sheets

FIG. 1A

N. meningitidis 1,733,738 to 1,736,684 DNA fragment "FIX" PCR

```
          gaccaaaccgacgaacgccgcgagaaagacaccttctagaacgaatttttcgccattttcggcatcgaccgcaaaaacg
1,733,795 ----+---------+---------+---------+---------+---------+---------+---------+----
          ctggtttggctgcttgcggcgctctttctgtggaagatcttgcttaaaaagcggtaaaagccgtagctggcgtttttgc
 (SEQ ID NO:1)
 coding: D  Q  T  D  E  R  R  E  K  D  T  F  *  N  E  F  F  A  I  F  G  I  D  R  K  N
                                                                               (SEQ ID NO:2)
```

FIG. 4A (1)
5'-..GTCAGCGGGGTC↓TGGTGTGGGAGGACGATGA<u>CTCGGC</u>AGACGACA..-3'
    (SEQ ID NO:5)
3'-..CAGTCGCCCC↑AGACCACACCCTCCTGCTACT<u>GAGCCG</u>TCTGCTGT..-5'

(2)
5'-PRIMER-->
3'-..CAGTCGCCCC↑(AGACCACACCCTCCTGCTACT<u>GAGCCG</u>TCTGCTGT..)-5'
    (SEQ ID NO:6)

(3)
5'-PRIMER..GTCAGCGGGGA.............................-3'
        (SEQ ID NO:7)
3'-........CAGTCGCCCC↑(AGACCACACCCTCCTGCTACT<u>GAGCCG</u>TCTG)-5'
                     10987654321 0987654321  =N21
        (SEQ ID NO:8)

(4)   (SEQ ID NO:9)

GTCAGCGGGGN<u>C</u>TGGTGTGGGAGGACGATGACTCGGCAGACGACA

FIG. 4B (1)
5'-...AAACTGGC<u>GCCGAG</u>CGTATGCCGCATGACCTTTCC↓CATCTTGGCT...-3'
         (SEQ ID NO:10)
3'-...TTTGACCG<u>CGGCTC</u>GCATACGGCGTACTGGAAA↑GGGTAGAACCGA...-5'

(2)
5'-PRIMER-->
3'-...........TTTGACCG<u>CGGCTC</u>GCATACGGCGTACTGGAAA↑....-5'
              (SEQ ID NO:11)

(3)
5'-PRIMER...AAACTGGC<u>GCCGAG</u>CGTATGCCGCATGACCTTTA..-3'
              (SEQ ID NO:12)
3'-.........TTTGACCG<u>CGGCTC</u>GCATACGGCGTACTGGAAA↑..-5'
                     1234567890123456789 =N19
              (SEQ ID NO:13)

(4) (SEQ ID NO:14)

AAACTGGCGCCGAGCGTATGCCGCATGACCT<u>T</u><u>T</u>N<u>CC</u>ATCTTGGCT
| 280    290    300    310 |

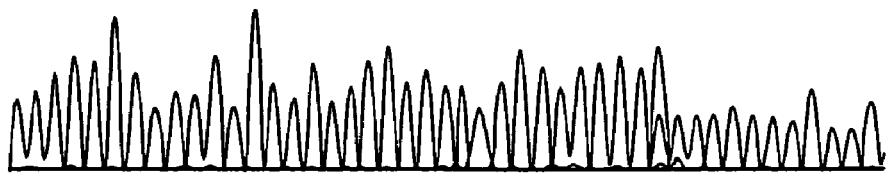

FIG. 4C-1

(1) NmeAIII
5'-..GT<u>GCCGAG</u>ATGCAAAATGAGACTCGGGGG↓GATC...-3'
   (SEQ ID NO:15)
3'-..CA<u>CGGCTC</u>TACGTTTTACTCTGAGCCC↑CCCTAG...-5'

(2) MmeI
5'-..GT<u>TCCGAC</u>ATGCAAAATGAGACTCGGGG↓G↓GATC...-3'
   (SEQ ID NO:16)
3'-..CA<u>AGGCTG</u>TACGTTTTACTCTGAGCC↑C↑CCCTAG...-5'

(3) NmeAIII
5'-..GT<u>GCCGAG</u>ATGCAAAATGAGACTCGGGA..-3'
   (SEQ ID NO:17)
3'-..CA<u>CGGCTC</u>TACGTTTTACTCTGAGCCC↑CCCTAG...-5'
   (SEQ ID NO:18)

(4) MmeI
5'-PRIMER..GT<u>TCCGAC</u>ATGCAAAATGAGACTCGGAA..-3'
        (SEQ ID NO:19)
3'-........CA<u>AGGCTG</u>TACGTTTTACTCTGAGCC↑C↑CCCTAG...-5'
        (SEQ ID NO:20)

pAII17-NmeAIII plasmid Restriction Map

FIG. 6-1

DNA Fragment encoding NmeAIII: 2814bp (SEQ ID NO:23)

```
ATGAAAACCCTGCTCCAACTCCAAACCGCCGCACAAAACTTCGCCGCCTA
CTACAAAGACCAAACCGACGAACGCCGCGAGAAAGACACCTTCTGGAACG
AATTTTTCGCCATTTTCGGCATCGACCGCAAAAACGTCGCCCACTTCGAA
TACCCCGTCAAAGACCCTGCCGACAACACCCAATTCGTCGATATATTTTG
GGAAGGCATCTTCCTTGCCGAACACAAATCCGCCAACAAAAACCTGACCA
AGGCCAAAGAGCAGGCGGAACGTTATTTACAGGAAATCGGGCGCACCAAG
CCCTCCGCGCTGCCCGAATATTACGCCGTCAGCGATTTTGCCCATTTCCA
CCTTTACCGCCGCGTACCTGAAGAAGGCGCAGAAAACCAATGGCAGTTCC
CTTTGGAAGAATTGCCTGAATACATCACGCGCGGCGTTTTCGACTTCATG
TTCGGCATCGAAGCCAAAGTCCGCCAAATTCAAGAAGAAGCCAACATTCA
AGCGGCGGCGACCATCGGCAGGCTGCACGACGCGCTCAAAGAAGAAGGCA
TTTACGAAGAACACGAGCTGCGCCTCTTCATCACGCGCCTGCTTTTCCTC
TTTTTTGCCGACGACAGCGCCGTTTTCCGGCGCAACTACCTTTTCCAAGA
CTTTTTAGAAAAACTGCAAAGAAGCCGACACGCTCGGCGACAAGCTCAATC
AACTCTTTGAATTTCTCAACACACCCGACCAAAAGCGCAGCAAGACCCAA
AGCGAAAAATTTAAAGGTTTCGAATACGTCAACGGCGGTCTTTTCAAAGA
ACGCCTGCGCACTTTCGACTTCACTGCCAAGCAGCACCGCGCCTTAATCG
ACTGCGGCAATTTCGACTGGCGCAACATCAGTCCAGAAATCTTCGGCACG
CTCTTCCAATCCGTCATGGACGCGCAAGAGCGGCGCGAAGCGGGCGCGCA
CTACACCGAAGCCGCCAATATCGACAAAGTCATCAACGGCCTTTTTTTAG
AAAACCTGCGTGCCGAATTTGAAGCCGTCAAAGCCCTCAAACGCGACAAA
GCCAAAAAACTCGCCGCCTTCTACCAAAAAATCCAAAACCTGCAATTCCT
CGACCCTGCCTGCGGCTGCGGCAACTTCCTTATCGTCGCCTACGACCGCA
TCCGCGCCCTTGAAGACGACATCATCGCCGAAGCCCTCAAAGACAAAGCA
GACGGCCTGTTCGACAGCCCGTCCGTCCAATGCCGTCTGAAACAGTTTCA
CGGCATCGAAATAGACGAATTTGCCGTCCTCATCGCCCGCACCGCCATGT
GGCTCAAAAACCACCAATGCAACATCCGCACACAAATCCGCTTCGACGGC
GAAGTCGCCTGCCATACGCTGCCGCTCGAAGACGCCGCCGAAATCATCCA
```

FIG. 6-2

```
CGCCAACAGCCTCCGCACACCTTGGCAGGCGGCGGACTACATCTTCGGCA
ATCCCCCTTTATCGGCTCGACCTACCAAACCAAAGAGCAGAAAAACGAC
CTCGAAAGCATCTGCGGCCATATCAAAGGCTACGGCCTGTTGGATTACGT
CTGCAACTGGTACGTCAAAGCCGCAGGCATCATGGCGCAGCATCCCCAAG
TTCAGACGGCATTTGTTTCCACCAATTCCATCTGCCAAGGCCAGCAGGTC
GAAATCCTCTGGGGCAGCCTTTTAAACCAAGGCATCGAAATCCACTTTGC
CCACCGCACCTTCCAATGGACGAGCCAAGCCGCAGGCAAAGCCGCCGTCC
ACTGCATCATCGTCGGCTTCCGCCAAAAGCCGCCAATGCCGTCTGAAAAA
ACCCTCTACGACTATCCCGACATCAAAGGCGAACCCGAAAAACACGCCGT
AGCCAACATCAATCCTTATCTGATCGATGCGCCCGATTTGATTATCGCCA
AGCGCAGCCGTCCCATACATTGCGAACCTGATATGGTCAACGGAAGCAAA
CCGACCGAAGGCGGCAACCTTATCCTTTCAACCGCCGAAAAAGATGCCCT
GATTGCCGCCGAACCCTTGGCGGAGCAATACATCCGCCCCTTTATCGGCG
CGGATGAGTTTCTCAACGGCAAAACCCGTTGGTGCCTGTGGTTTCACGGC
GTATCCGATGTCAAACGCAACCACGACCTGAAACAAATGCCCCAAGTTCA
AGCCCGTATTCAGGCGGTCAAAACCATGCGCGAAGCCAGCAGCGACAAAC
AAACTCAAAAAGATGCAGCAACCCCGTGGCTTTTTCAAAAAAATCCGCCAG
CCTTCAGACGGCAATTATCTGATTATTCCGAGCGTGTCGTCTGAAAGCCG
CCGTTTCATCCCCATCGGTTATCTGTCGTTTGAAACAGTTGTCAGCAATC
TGGCATTTATCCTTCCAAACGCCACCCTCTACCACTTCGGCATCCTCAGC
TCCACCATGCACAACGCCTTTATGCGTACCGTTGCAGGTCGTCTGAAAAG
CGATTATCGCTACTCTAATACCGTCGTGTACAACAACTTCCCCCTTCCCCG
AAAGCTGCCGGTTGCCGTCTGAAAACGACCGCCCCGACCCGCTCCGCGCC
GCCGTCGAAGCCGCCGCCCAAACCGTCCTCGACGCGCGCGGACAATACCG
CCGAGAAGCGCAGGAAGCCGGTTTGCCCGAGCCGACCCTCGCCGAACTCT
ATGCGCCCGACGCAGGCTATACCGCCCTCGACAAAGCCCACGCCACCCTC
GACAAGGCAGTCGATAAAGCCTACGGCTACAAAACAGGCAAAAATACCGA
CGACGAGGCAGAACGCGTCGCCTTCCTGTTCGAGCTGTACCGCAAGGCGG
CGGCAATTGCGTAG
```

FIG. 7

NmeAIII amino acid sequence > 937 aa (SEQ ID NO:24)

```
MKTLLQLQTA AQNFAAYYKD QTDERREKDT FWNEFFAIFG IDRKNVAHFE
YPVKDPADNT QFVDIFWEGI FLAEHKSANK NLTKAKEQAE RYLQEIGRTK
PSALPEYYAV SDFAHFHLYR RVPEEGAENQ WQFPLEELPE YITRGVFDFM
FGIEAKVRQI QEEANIQAAA TIGRLHDALK EEGIYEEHEL RLFITRLLFL
FFADDSAVFR RNYLFQDFLE NCKEADTLGD KLNQLFEFLN TPDQKRSKTQ
SEKFKGFEYV NGGLFKERLR TFDFTAKQHR ALIDCGNFDW RNISPEIFGT
LFQSVMDAQE RREAGAHYTE AANIDKVING LFLENLRAEF EAVKALKRDK
AKKLAAFYQK IQNLQFLDPA CGCGNFLIVA YDRIRALEDD IIAEALKDKA
DGLFDSPSVQ CRLKQFHGIE IDEFAVLIAR TAMWLKNHQC NIRTQIRFDG
EVACHTLPLE DAAEIIHANS LRTPWQAADY IFGNPPFIGS TYQTKEQKND
LESICGHIKG YGLLDYVCNW YVKAAGIMAQ HPQVQTAFVS TNSICQGQQV
EILWGSLLNQ GIEIHFAHRT FQWTSQAAGK AAVHCIIVGF RQKPPMPSEK
TLYDYPDIKG EPEKHAVANI NPYLIDAPDL IIAKRSRPIH CEPDMVNGSK
PTEGGNLILS TAEKDALIAA EPLAEQYIRP FIGADEFLNG KTRWCLWFHG
VSDVKRNHDL KQMPQVQARI QAVKTMREAS SDKQTQKDAA TPWLFQKIRQ
PSDGNYLIIP SVSSESRRFI PIGYLSFETV VSNLAFILPN ATLYHFGILS
STMHNAFMRT VAGRLKSDYR YSNTVVYNNF PFPESCRLPS ENDRPDPLRA
AVEAAAQTVL DARGQYRREA QEAGLPEPTL AELYAPDAGY TALDKAHATL
DKAVDKAYGY KTGKNTDDEA ERVAFLFELY RKAAAIA
```

FIG. 8-1

NmeAIII-pAII17 construct: DNA Sequence (SEQ ID NO:25)

```
1    AGCTTTAATG CGGTAGTTTA TCACAGTTAA ATTGCTAACG CAGTCAGGCA
51   CCGTGTATGA AATCTAACAA TGCGCTCATC GTCATCCTCG GCACCGTCAC
101  CCTGGATGCT GTAGGCATAG GCTTGGTTAT GCCGGTACTG CCGGGCCTCT
151  TGCGGGATAT CCGGATATAG TTCCTCCTTT CAGCAAAAAA CCCCTCAAGA
201  CCCGTTTAGA GGCCCCAAGG GGTTATGCTA GTTATTGCTC AGCGGTGGCA
251  GCAGCCAACT CAGCTTCCTT TCGGGCTTTG TTAGCAGCCG GATCCGTCGA
301  CCCTACGCAA TTGCTTTTGC GGAGATGACG GGGTTTTAGG GTGAAGATGG
351  TGGGAGTTGG TGGGAGTTGG TGGGCTGAAG CCCACCCTAC GCAACTATCC
401  TACGCAACTA CTACGCAACT ACTACGCAAC TACTACGCAA TTGCCGCCGC
451  CTTGCGGTAC AGCTCGAACA GGAAGGCGAC GCGTTCTGCC TCGTCGTCGG
501  TATTTTTGCC TGTTTTGTAG CCGTAGGCTT TATCGACTGC CTTGTCGAGG
551  GTGGCGTGGG CTTTGTCGAG GCGGTATAG CCTGCGTCGG GCGCATAGAG
601  TTCGGCGAGG GTCGGCTCGG GCAAACCGGC TTCCTGCGCT TCTCGGCGGT
651  ATTGTCCGCG CGCGTCGAGG ACGGTTTGGG CGGCGGCTTC GACGGCGGCG
701  CGGAGCGGGT CGGGGCGGTC GTTTTCAGAC GGCAACCGGC AGCTTTCGGG
751  GAAGGGGAAG TTGTTGTACA CGACGGTATT AGAGTAGCGA TAATCGCTTT
801  TCAGACGACC TGCAACGGTA CGCATAAAGG CGTTGTGCAT GGTGGAGCTG
851  AGGATGCCGA AGTGGTAGAG GGTGGCGTTT GGAAGGATAA ATGCCAGATT
901  GCTGACAACT GTTTCAAACG ACAGATAACC GATGGGGATG AAACGGCGGC
951  TTTCAGACGA CACGCTCGGA ATAATCAGAT AATTGCCGTC TGAAGGCTGG
1001 CGGATTTTTT GAAAAAGCCA CGGGGTTGCT GCATCTTTTT GAGTTTGTTT
1051 GTCGCTGCTG GCTTCGCGCA TGGTTTTGAC CGCCTGAATA CGGGCTTGAA
1101 CTTGGGGCAT TTGTTTCAGG TCGTGGTTGC GTTTGACATC GGATACGCCG
1151 TGAAACCACA GGCACCAACG GGTTTTGCCG TTGAGAAACT CATCCGCGCC
1201 GATAAAGGGG CGGATGTATT GCTCCGCCAA GGGTCGGCG GCAATCAGGG
1251 CATCTTTTTC GGCGGTTGAA AGGATAAGGT TGCCGCCTTC GGTCGGTTTG
1301 CTTCCGTTGA CCATATCAGG TTCGCAATGT ATGGGACGGC TGCGCTTGGC
1351 GATAATCAAA TCGGGCGCAT CGATCAGATA AGGATTGATG TTGGCTACGG
1401 CGTGTTTTTC GGGTTCGCCT TGATGTCGG GATAGTCGTA GAGGGTTTTT
1451 TCAGACGGCA TTGGCGGCTT TTGGCGGAAG CCGACGATGA TGCAGTGGAC
1501 GGCGGCTTTG CCTGCGGCTT GGCTCGTCCA TTGGAAGGTG CGGTGGGCAA
1551 AGTGGATTTC GATGCCTTGG TTTAAAAGGC TGCCCCAGAG GATTTCGACC
1601 TGCTGGCCTT GGCAGATGGA ATTGGTGGAA ACAAATGCCG TCTGAACTTG
```

FIG. 8-2

```
1651 GGGATGCTGC GCCATGATGC CTGCGGCTTT GACGTACCAG TTGCAGACGT
1701 AATCCAACAG GCCGTAGCCT TTGATATGGC CGCAGATGCT TTCGAGGTCG
1751 TTTTTCTGCT CTTTGGTTTG GTAGGTCGAG CCGATAAAGG GGGGATTGCC
1801 GAAGATGTAG TCCGCCGCCT GCCAAGGTGT GCGGAGGCTG TTGGCGTGGA
1851 TGATTTCGGC GGCGTCTTCG AGCGGCAGCG TATGGCAGGC GACTTCGCCG
1901 TCGAAGCGGA TTTGTGTGCG GATGTTGCAT TGGTGGTTTT TGAGCCACAT
1951 GGCGGTGCGG GCGATGAGGA CGGCAAATTC GTCTATTTCG ATGCCGTGAA
2001 ACTGTTTCAG ACGGCATTGG ACGGACGGGC TGTCGAACAG GCCGTCTGCT
2051 TTGTCTTTGA GGGCTTCGGC GATGATGTCG TCTTCAAGGG CGCGGATGCG
2101 GTCGTAGGCG ACGATAAGGA AGTTGCCGCA GCCGCAGGCA GGGTCGAGGA
2151 ATTGCAGGTT TTGGATTTTT TGGTAGAAGG CGGCGAGTTT TTTGGCTTTG
2201 TCGCGTTTGA GGGCTTTGAC GGCTTCAAAT TCGGCACGCA GGTTTTCTAA
2251 AAAAAGGCCG TTGATGACTT TGTCGATATT GGCGGCTTCG GTGTAGTGCG
2301 CGCCCGCTTC GCGCCGCTCT TGCGCGTCCA TGACGGATTG GAAGAGCGTG
2351 CCGAAGATTT CTGGACTGAT GTTGCGCCAG TCGAAATTGC CGCAGTCGAT
2401 TAAGGCGCGG TGCTGCTTGG CAGTGAAGTC GAAAGTGCGC AGGCGTTCTT
2451 TGAAAAGACC GCCGTTGACG TATTCGAAAC CTTTAAATTT TTCGCTTTGG
2501 GTCTTGCTGC GCTTTTGGTC GGGTGTGTTG AGAAATTCAA AGAGTTGATT
2551 GAGCTTGTCG CCGAGCGTGT CGGCTTCTTT GCAGTTTTCT AAAAAGTCTT
2601 GGAAAAGGTA GTTGCGCCGG AAAACGGCGC TGTCGTCGGC AAAAAAGAGG
2651 AAAAGCAGGC GCGTGATGAA GAGGCGCAGC TCGTGTTCTT CGTAAATGCC
2701 TTCTTCTTTG AGCGCGTCGT GCAGCCTGCC GATGGTCGCC GCCGCTTGAA
2751 TGTTGGCTTC TTCTTGAATT TGGCGGACTT TGGCTTCGAT GCCGAACATG
2801 AAGTCGAAAA CGCCGCGCGT GATGTATTCA GGCAATTCTT CCAAAGGGAA
2851 CTGCCATTGG TTTTCTGCGC CTTCTTCAGG TACGCGGCGG TAAAGGTGGA
2901 AATGGGCAAA ATCGCTGACG GCGTAATATT CGGGCAGCGC GGAGGGCTTG
2951 GTGCGCCCGA TTTCCTGTAA ATAACGTTCC GCCTGCTCTT TGGCCTTGGT
3001 CAGGTTTTTG TTGGCGGATT TGTGTTCGGC AAGGAAGATG CCTTCCCAAA
3051 ATATATCGAC GAATTGGGTG TTGTCGGCAG GGTCTTTGAC GGGGTATTCG
3101 AAGTGGGCGA CGTTTTTGCG GTCGATGCCG AAAATGGCGA AAAATTCGTT
3151 CCAGAAGGTG TCTTTCTCGC GGCGTTCGTC GGTTTGGTCT TTGTAGTAGG
3201 CGGCGAAGTT TTGTGCGGCG GTTTGGAGTT GGAGCAGGGT TTTCATATGT
3251 ATATCTCCTT CTTAAAGTTA AACAAAATTA TTTCTAGAGG GGAATTGTTA
3301 TCCGCTCACA ATTCCCCTAT AGTGAGTCGT ATTAATTTCG CGGGATCGAG
```

FIG. 8-3

```
3351 ATCCCCGGGA ATTAATTCCG ATCCCCAATT CCTGGCAGTT TATGGCGGGC
3401 GTCCTGCCCG CCACCCTCCG GGCCGTTGCT TCGCAACGTT CAAATCCGCT
3451 CCCGGCGGAT TTGTCCTACT CAGGAGAGCG TTCACCGACA AACAACAGAT
3501 AAAACGAAAG GCCCAGTCTT TCGACTGAGC CTTTCGTTTT ATTTGATGCC
3551 TGGAATTAAT TCCTGGCAGT TTATGGCGGG CGTCCTGCCC GCCACCCTCC
3601 GGGCCGTTGC TTCGCAACGT TCAAATCCGC TCCCGGCGGA TTTGTCCTAC
3651 TCAGGAGAGC GTTCACCGAC AAACAACAGA TAAAACGAAA GGCCCAGTCT
3701 TTCGACTGAG CCTTTCGTTT TATTTGATGC CTGGAATTAA TTCCTGGCAG
3751 TTTATGGCGG GCGTCCTGCC CGCCACCCTC CGGGCCGTTG CTTCGCAACG
3801 TTCAAATCCG CTCCCGGCGG ATTTGTCCTA CTCAGGAGAG CGTTCACCGA
3851 CAAACAACAG ATAAAACGAA AGGCCCAGTC TTTCGACTGA GCCTTTCGTT
3901 TTATTTGATG CCTGGAATTA ATTCCTGGCA GTTTATGGCG GCGTCCTGC
3951 CCGCCACCCT CCGGGCCGTT GCTTCGCAAC GTTCAAATCC GCTCCCGGCG
4001 GATTTGTCCT ACTCAGGAGA GCGTTCACCG ACAAACAACA GATAAAACGA
4051 AAGGCCCAGT CTTTCGACTG AGCCTTTCGT TTTATTTGAT GCCTGGAATT
4101 GGGAATTAAT TCTTGAAGAC GAAAGGGCGG CATGCACCAT TCCTTGCGGC
4151 GGCGGTGCTC AACGGCCTCA ACCTACTACT GGGCTGCTTC CTAATGCAGG
4201 AGTCGCATAA GGGAGAGCGT CGAGATCCGG GACACCATCG AATGGCGCAA
4251 AACCTTTCGC GGTATGGCAT GATAGCGCCC GGAAGAGAGT CAATTCAGGG
4301 TGGTGAATGT GAAACCAGTA ACGTTATACG ATGTCGCAGA GTATGCCGGT
4351 GTCTCTTATC AGACCGTTTC CCGCGTGGTG AACCAGGCCA GCCACGTTTC
4401 TGCGAAAACG CGGGAAAAAG TGGAAGCGGC GATGGCGGAG CTGAATTACA
4451 TTCCCAACCG CGTGGCACAA CAACTGGCGG GCAAACAGTC GTTGCTGATT
4501 GGCGTTGCCA CCTCCAGTCT GGCCCTGCAC GCGCCGTCGC AAATTGTCGC
4551 GGCGATTAAA TCTCGCGCCG ATCAACTGGG TGCCAGCGTG GTGGTGTCGA
4601 TGGTAGAACG AAGCGGCGTC GAAGCCTGTA AAGCGGCGGT GCACAATCTT
4651 CTCGCGCAAC GCGTCAGTGG GCTGATCATT AACTATCCGC TGGATGACCA
4701 GGATGCCATT GCTGTGGAAG CTGCCTGCAC TAATGTTCCG GCGTTATTTC
4751 TTGATGTCTC TGACCAGACA CCCATCAACA GTATTATTTT CTCCCATGAA
4801 GACGGTACGC GACTGGGCGT GGAGCATCTG GTCGCATTGG GTCACCAGCA
4851 AATCGCGCTG TTAGCGGGCC CATTAAGTTC TGTCTCGGCG CGTCTGCGTC
4901 TGGCTGGCTG GCATAAATAT CTCACTCGCA ATCAAATTCA GCCGATAGCG
4951 GAACGGGAAG GCGACTGGAG TGCCATGTCC GGTTTTCAAC AAACCATGCA
5001 AATGCTGAAT GAGGGCATCG TTCCCACTGC GATGCTGGTT GCCAACGATC
```

FIG. 8-4

```
5051  AGATGGCGCT GGGCGCAATG CGCGCCATTA CCGAGTCCGG GCTGCGCGTT
5101  GGTGCGGATA TCTCGGTAGT GGGATACGAC GATACCGAAG ACAGCTCATG
5151  TTATATCCCG CCGTCAACCA CCATCAAACA GGATTTTCGC CTGCTGGGGC
5201  AAACCAGCGT GGACCGCTTG CTGCAACTCT CTCAGGGCCA GGCGGTGAAG
5251  GGCAATCAGC TGTTGCCCGT CTCACTGGTG AAAAGAAAAA CCACCCTGGC
5301  GCCCAATACG CAAACCGCCT CTCCCCGCGC GTTGGCCGAT TCATTAATGC
5351  AGCTGGCACG ACAGGTTTCC CGACTGGAAA GCGGGCAGTG AGCGCAACGC
5401  AATTAATGTG AGTTAGCTCA CTCATTAGGC CGGGATCTCG ACCGATGCCC
5451  TTGAGAGCCT TCAACCCAGT CAGCTCCTTC CGGTGGGCGC GGGGCATGAC
5501  TATCGTCGCC GCACTTATGA CTGTCTTCTT TATCATGCAA CTCGTAGGAC
5551  AGGTGCCGGC AGCGCTCTGG GTCATTTTCG GCGAGGACCG CTTTCGCTGG
5601  AGCGCGACGA TGATCGGCCT GTCGCTTGCG GTATTCGGAA TCTTGCACGC
5651  CCTCGCTCAA GCCTTCGTCA CTGGTCCCGC CACCAAACGT TTCGGCGAGA
5701  AGCAGGCCAT TATCGCCGGC ATGGCGGCCG ACGCGCTGGG CTACGTCTTG
5751  CTGGCGTTCG CGACGCGAGG CTGGATGGCC TTCCCCATTA TGATTCTTCT
5801  CGCTTCCGGC GGCATCGGGA TGCCCGCGTT GCAGGCCATG CTGTCCAGGC
5851  AGGTAGATGA CGACCATCAG GGACAGCTTC AAGGATCGCT CGCGGCTCTT
5901  ACCAGCCTAA CTTCGATCAC TGGACCGCTG ATCGTCACGG CGATTTATGC
5951  CGCCTCGGCG AGCACATGGA ACGGGTTGGC ATGGATTGTA GGCGCCGCCC
6001  TATACCTTGT CTGCCTCCCC GCGTTGCGTC GCGGTGCATG GAGCCGGGCC
6051  ACCTCGACCT GAATGGAAGC CGGCGGCACC TCGCTAACGG ATTCACCACT
6101  CCAAGAATTG GAGCCAATCA ATTCTTGCGG AGAACTGTGA ATGCGCAAAC
6151  CAACCCTTGG CAGAACATAT CCATCGCGTC CGCCATCTCC AGCAGCCGCA
6201  CGCGGCGCAT CTCGGGCAGC GTTGGGTCCT GGCCACGGGT GCGCATGATC
6251  GTGCTCCTGT CGTTGAGGAC CCGGCTAGGC TGGCGGGGTT GCCTTACTGG
6301  TTAGCAGAAT GAATCACCGA TACGCGAGCG AACGTGAAGC GACTGCTGCT
6351  GCAAAACGTC TGCGACCTGA GCAACAACAT GAATGGTCTT CGGTTTCCGT
6401  GTTTCGTAAA GTCTGGAAAC GCGGAAGTCA GCGCCCTGCA CCATTATGTT
6451  CCGGATCTGC ATCGCAGGAT GCTGCTGGCT ACCCTGTGGA ACACCTACAT
6501  CTGTATTAAC GAAGCGCTGG CATTGACCCT GAGTGATTTT TCTCTGGTCC
6551  CGCCGCATCC ATACCGCCAG TTGTTTACCC TCACAACGTT CCAGTAACCG
6601  GGCATGTTCA TCATCAGTAA CCCGTATCGT GAGCATCCTC TCTCGTTTCA
6651  TCGGTATCAT TACCCCCATG AACAGAAATT CCCCCTTACA CGGAGGCATC
6701  AAGTGACCAA ACAGGAAAAA ACCGCCCTTA ACATGGCCCG CTTTATCAGA
```

FIG. 8-5

```
6751 AGCCAGACAT TAACGCTTCT GGAGAAACTC AACGAGCTGG ACGCGGATGA
6801 ACAGGCAGAC ATCTGTGAAT CGCTTCACGA CCACGCTGAT GAGCTTTACC
6851 GCAGCTGCCT CGCGCGTTTC GGTGATGACG GTGAAAACCT CTGACACATG
6901 CAGCTCCCGG AGACGGTCAC AGCTTGTCTG TAAGCGGATG CCGGGAGCAG
6951 ACAAGCCCGT CAGGGCGCGT CAGCGGGTGT TGGCGGGTGT CGGGGCGCAG
7001 CCATGACCCA GTCACGTAGC GATAGCGGAG TGTATACTGG CTTAACTATG
7051 CGGCATCAGA GCAGATTGTA CTGAGAGTGC ACCATATATG CGGTGTGAAA
7101 TACCGCACAG ATGCGTAAGG AGAAAATACC GCATCAGGCG CTCTTCCGCT
7151 TCCTCGCTCA CTGACTCGCT GCGCTCGGTC GTTCGGCTGC GGCGAGCGGT
7201 ATCAGCTCAC TCAAAGGCGG TAATACGGTT ATCCACAGAA TCAGGGGATA
7251 ACGCAGGAAA GAACATGTGA GCAAAAGGCC AGCAAAAGGC CAGGAACCGT
7301 AAAAAGGCCG CGTTGCTGGC GTTTTTCCAT AGGCTCCGCC CCCCTGACGA
7351 GCATCACAAA AATCGACGCT CAAGTCAGAG GTGGCGAAAC CCGACAGGAC
7401 TATAAAGATA CCAGGCGTTT CCCCCTGGAA GCTCCCTCGT GCGCTCTCCT
7451 GTTCCGACCC TGCCGCTTAC CGGATACCTG TCCGCCTTTC TCCCTTCGGG
7501 AAGCGTGGCG CTTTCTCATA GCTCACGCTG TAGGTATCTC AGTTCGGTGT
7551 AGGTCGTTCG CTCCAAGCTG GGCTGTGTGC ACGAACCCCC CGTTCAGCCC
7601 GACCGCTGCG CCTTATCCGG TAACTATCGT CTTGAGTCCA ACCCGGTAAG
7651 ACACGACTTA TCGCCACTGG CAGCAGCCAC TGGTAACAGG ATTAGCAGAG
7701 CGAGGTATGT AGGCGGTGCT ACAGAGTTCT TGAAGTGGTG GCCTAACTAC
7751 GGCTACACTA GAAGGACAGT ATTTGGTATC TGCGCTCTGC TGAAGCCAGT
7801 TACCTTCGGA AAAAGAGTTG GTAGCTCTTG ATCCGGCAAA CAAACCACCG
7851 CTGGTAGCGG TGGTTTTTTT GTTTGCAAGC AGCAGATTAC GCGCAGAAAA
7901 AAAGGATCTC AAGAAGATCC TTTGATCTTT TCTACGGGGT CTGACGCTCA
7951 GTGGAACGAA AACTCACGTT AAGGGATTTT GGTCATGAGA TTATCAAAAA
8001 GGATCTTCAC CTAGATCCTT TTAAATTAAA AATGAAGTTT TAAATCAATC
8051 TAAAGTATAT ATGAGTAAAC TTGGTCTGAC AGTTACCAAT GCTTAATCAG
8101 TGAGGCACCT ATCTCAGCGA TCTGTCTATT TCGTTCATCC ATAGTTGCCT
8151 GACTCCCCGT CGTGTAGATA ACTACGATAC GGGAGGGCTT ACCATCTGGC
8201 CCCAGTGCTG CAATGATACC GCGAGACCCA CGCTCACCGG CTCCAGATTT
8251 ATCAGCAATA AACCAGCCAG CCGGAAGGGC CGAGCGCAGA AGTGGTCCTG
8301 CAACTTTATC CGCCTCCATC CAGTCTATTA ATTGTTGCCG GGAAGCTAGA
8351 GTAAGTAGTT CGCCAGTTAA TAGTTTGCGC AACGTTGTTG CCATTGCTGC
8401 AGGCATCGTG GTGTCACGCT CGTCGTTTGG TATGGCTTCA TTCAGCTCCG
```

FIG. 8-6

```
8451  GTTCCCAACG ATCAAGGCGA GTTACATGAT CCCCCATGTT GTGCAAAAAA
8501  GCGGTTAGCT CCTTCGGTCC TCCGATCGTT GTCAGAAGTA AGTTGGCCGC
8551  AGTGTTATCA CTCATGGTTA TGGCAGCACT GCATAATTCT CTTACTGTCA
8601  TGCCATCCGT AAGATGCTTT TCTGTGACTG GTGAGTACTC AACCAAGTCA
8651  TTCTGAGAAT AGTGTATGCG GCGACCGAGT TGCTCTTGCC CGGCGTCAAC
8701  ACGGGATAAT ACCGCGCCAC ATAGCAGAAC TTTAAAAGTG CTCATCATTG
8751  GAAAACGTTC TTCGGGGCGA AAACTCTCAA GGATCTTACC GCTGTTGAGA
8801  TCCAGTTCGA TGTAACCCAC TCGTGCACCC AACTGATCTT CAGCATCTTT
8851  TACTTTCACC AGCGTTTCTG GGTGAGCAAA AACAGGAAGG CAAAATGCCG
8901  CAAAAAAGGG AATAAGGGCG ACACGGAAAT GTTGAATACT CATACTCTTC
8951  CTTTTTCAAT ATTATTGAAG CATTTATCAG GGTTATTGTC TCATGAGCGG
9001  ATACATATTT GAATGTATTT AGAAAAATAA ACAAATAGGG GTTCCGCGCA
9051  CATTTCCCCG AAAAGTGCCA CCTGACGTCT AAGAAACCAT TATTATCATG
9101  ACATTAACCT ATAAAAATAG GCGTATCACG AGGCCCTTTC GTCTTCAAGA
9151  ATT
```

RECOMBINANT TYPE II RESTRICTION ENDONUCLEASE, NMEAIII, AND A PROCESS FOR PRODUCING THE SAME

CROSS REFERENCE

This application is a §371 application of international application number PCT/US2007/088522 filed on 21 Dec. 2007, which claims priority from U.S. provisional application No. 60/877,265 filed on 27 Dec. 2006, herein incorporated by reference.

BACKGROUND

Restriction endonucleases are enzymes that occur naturally in certain unicellular microbes—mainly bacteria and archaea—and that function to protect these organisms from infections by viruses and other parasitic DNA elements. Restriction endonucleases bind to specific sequences of nucleotides ('recognition sequence') in double-stranded DNA molecules (dsDNA) and cleave the DNA, usually within or close to the sequence, disrupting the DNA and triggering its destruction. Restriction endonucleases commonly occur with one or more companion enzymes termed modification methyltransferases. Methyltransferases bind to the same sequences in dsDNA as the restriction endonucleases they accompany, but instead of cleaving the DNA, they alter it by the addition of a methyl group to one of the bases within the sequence. This methylation ('modification') prevents the restriction endonuclease from binding to that site thereafter, rendering the site resistant to cleavage. Methyltransferases function as cellular antidotes to the restriction endonucleases they accompany, protecting the cell's own DNA from destruction by its restriction endonucleases. Together, a restriction endonuclease and its companion modification methyltransferase(s) form a restriction-modification (R-M) system, an enzymatic partnership that accomplishes for microbes what the immune system accomplishes, in some respects, for multicellular organisms.

A large and varied class of restriction endonucleases has been classified as 'Type II' restriction endonucleases. These enzymes cleave DNA at defined positions, and in purified form can be used to cut DNA molecules into precise fragments for gene cloning and analysis. The biochemical precision of Type II restriction endonucleases far exceeds anything achievable by chemical methods, making these enzymes the reagents sine qua non of molecular biology laboratories. In this capacity, as molecular tools for gene dissection, Type II restriction endonucleases have had a profound impact on the life sciences in the past 35 years, transforming the academic and commercial arenas, alike. Their utility has spurred a continuous search for new restriction endonucleases, and a large number have been found (Roberts and Macelis, *Nucl. Acids Res.* 29:268-269 (2001)). (REBASE®, http://rebase.neb.com/rebase). Today, Type II endonucleases, recognizing more than 250 unique DNA recognition sequences, are known among the several thousand enzymes that have been characterized. Concomitantly, the production and purification of these enzymes has been improved by the cloning and over-expression of the genes that encode them in non-natural production strain host cells such as *E. coli*.

Since the various restriction enzymes appear to perform similar biological roles, in much the same ways, it might be thought that they would resemble one another closely in amino acid sequence and behavior. Experience shows this not to be true, however. Surprisingly, far from resembling one another, most Type II restriction enzymes appear unique, resembling neither other restriction enzymes nor any other known kind of protein. Type II restriction endonucleases seem to have arisen independently of one another for the most part during evolution, and to have done so hundreds of times, so that today's enzymes represent a heterogeneous collection rather than a discrete family. Some restriction endonucleases act as homodimers, some as monomers, and others as heterodimers. Some bind symmetric sequences, others asymmetric sequences; some bind continuous sequences, others discontinuous sequences; some bind unique sequences, others multiple sequences. Some are accompanied by a single methyltransferase, others by two, and yet others by none at all. When two methyltransferases are present, sometimes they are separate proteins, and at other times they are fused. The orders and orientations of restriction and modification genes vary, with all possible organizations occurring. Several kinds of methyltransferases exist, some methylating adenines (m6A-MTases), others methylating cytosines at the N-4 position (m4C-MTases), or at the 5 position (m5C-MTases). Usually there is no way of predicting, a priori, which modifications will block a particular restriction endonuclease, which kind(s) of methyltransferases(s) will accompany that restriction endonuclease in any specific instance, nor what their gene orders or orientations will be.

A hallmark of restriction endonucleases is their great variability in amino acid sequence and catalytic behavior; each occurs in unique enzymatic association, adapted to unique microbial circumstances; and each presents the experimenter with a unique challenge. Sometimes a restriction endonuclease can be cloned and over-expressed in a straightforward manner but more often than not it cannot, and what works well for one enzyme can work not at all for the next. Success with one is no guarantee of success with another.

SUMMARY

In an embodiment of the invention, a protein is provided that has an amino acid sequence characterized by at least 50% sequence identity, more particularly at least 80% sequence identity, more particularly at least 90% sequence identity, with SEQ ID NO:24, the protein having restriction endonuclease activity. The protein is further characterized as being capable of recognizing a sequence consisting of 5'-GCCGAG-3' within the DNA and cleaving the double-stranded DNA substrate predominantly at 19 nucleotides on one strand and 21 nucleotides on the complementary strand from the recognition site (21/19). In an additional embodiment, a DNA fragment encoding the protein is provided and also a vector that includes the DNA fragment, and a host cell containing the vector for expressing the protein.

In an embodiment of the invention, a method is provided that includes the steps of: creating a DNA tag by cleaving a target DNA with the protein described above; for use in sequencing applications such as for a unique identifier for paired end sequencing of DNA or for serial analysis of gene expression.

BRIEF DESCRIPTION OF THE DRAWINGS

FIG. 1A shows a region of *Neisseria meningitidis* DNA sequence (SEQ ID NO:1) which contains a stop codon at the 13$^{th}$ amino acid position of the sequence fragment shown.

FIG. 1B shows a pAII17 plasmid containing the *N. meningitidis* 1,733,738 to 1,736,684 DNA fragment in which the stop codon is replaced with tryptophan by changing "tag" nucleotides to "tgg". The primers (SEQ ID NOS:3 and 4) used to amplify the pAII17 plasmid have a phosphate (P) at the 5' end. The product of amplification is a linear molecule with phosphate groups at the 5' ends of each strand so that ligation can occur to generate a DNA encoding an NmeAIII carrying a point mutation. This was achieved using a Phusion site directed mutagenesis kit (New England Biolabs, Inc. (NEB), Ipswich, Mass.).

Figure 2:
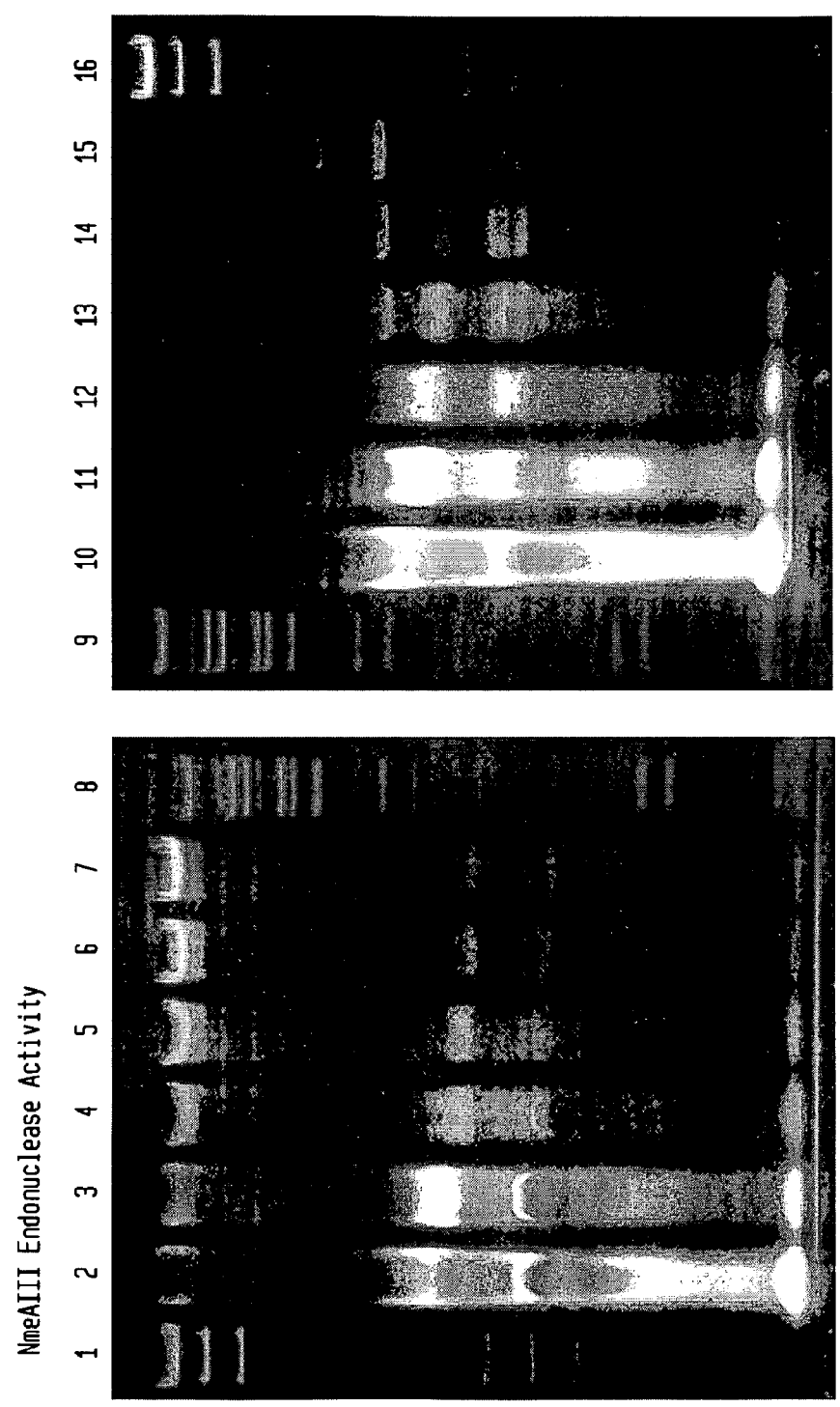

FIG. 2 shows NmeAIII endonuclease activity of a protein encoded by a DNA sequence corresponding to the modified extended NmeAIII 1791 reading frame, in which the stop codon at position 32 is replaced by a tryptophan.

Lanes 1 and 16 contain size standards: lambda-HindIII and PhiX174-HaeIII.
Lanes 2 to 7 contain serial dilution of NmeAIII crude extract with lambda DNA, from 8 µl per 50 µl reaction (lane 2) to 0.25 µl crude extract per 50 µl reaction (lane 7).
Lanes 8 and 9: size standards—lambda BstEII and pBR322-MspI.

Figure 3A:
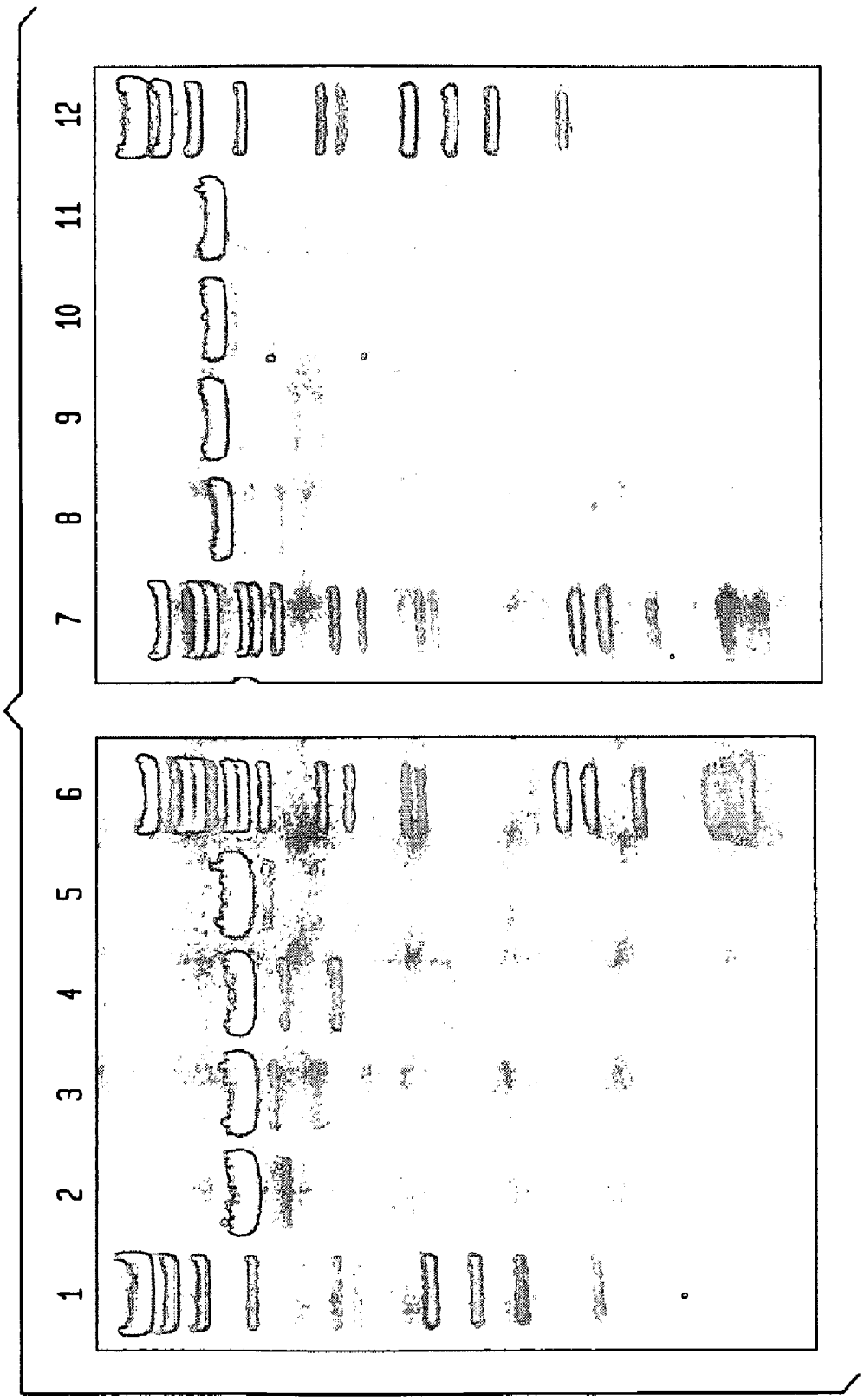

FIG. 3A shows the mapping of NmeAIII recognition sites.
Lanes 2-5 contain pBR322 DNA cleaved by NmeAIII and each of the following restriction enzymes: ClaI (lane 2), NruI (lane 3), NdeI (lane 4) and PstI (lane 5).
Lane 8-11: PhiX174 cleaved by NmeAIII and each of the following restriction enzymes: PstI (lane 8), SspI (lane 9), NciI (lane 10) and StuI (lane 11).
Lanes 1 and 12: lambda-HindIII, PhiX-HaeIII size standards.
Lanes 6 and 7: lambda BstEII, pBR322-MspI size standards.

Figure 3B:
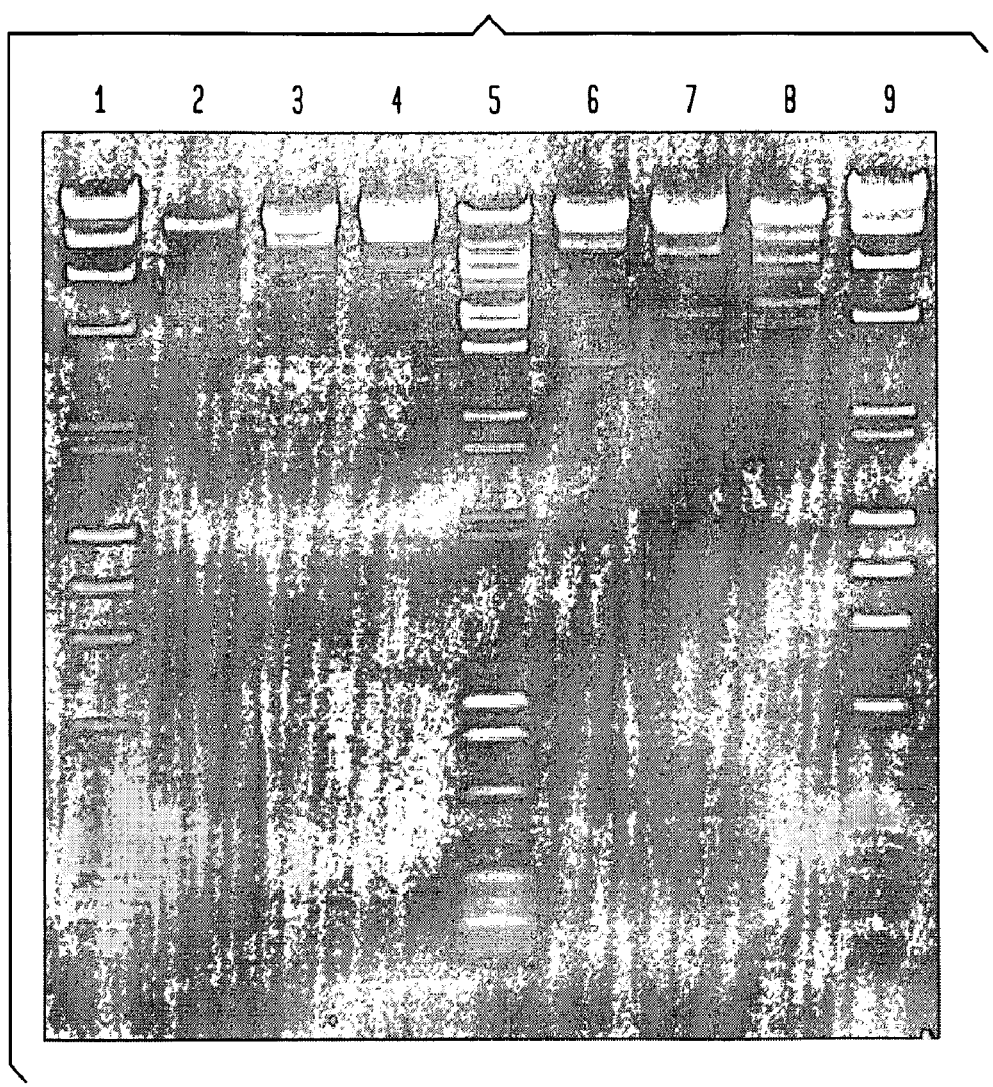

FIG. 3B shows the mapping of NmeAIII recognition sites.
Lanes 2-4 and 6-8 contain pBC4 DNA cleaved by NmeAIII and each of the following restriction enzymes: NdeI (lane 2), AvrII (lane 3), PmeI (lane 4), AscI (lane 6), SpeI (lane 7) and EcoRV (lane 8).
Lanes 1 and 9 contain lambda-HindIII and PhiX-HaeIII DNA size standards.
Lane 5 contains lambda-BstEII and pBR322-MspI DNA size standards.

FIG. 4A shows how the location of the NmeAIII cleavage site is determined on the top 5'-GCCGAG-3' strand.

DNA (pBC4) having an NmeAIII recognition site at position 3741 and a convenient primer (3475-3497) (SEQ ID NO:5) was cut with NmeAIII, yielding ends indicated by the arrows (1). The bottom strand (SEQ ID NO:6) served as the template for dideoxy DNA sequencing extension (2). The primer was annealed and extended through the NmeAIII site. When the reaction reached the end of the molecule opposite the NmeAIII cleavage site, the Taq polymerase added an extra A base (3) (SEQ ID NO:7). SEQ ID NO:8 includes in parentheses an additional sequence that is generally cleaved and therefore not reflected in the extended primer sequence. A sequencing profile of NmeAIII was generated for NmeAIII cleaved pBC4 DNA (ABI377 Sequencer) showing the cleavage site (4) (SEQ ID NO:9). The height of the peaks denotes the frequency of occurrence of a base in the fragment population. At position "N" the height of the peaks is dramatically reduced because of the enzyme cleavage site. Low amounts of single bases can be detected past the cleavage site because the enzyme cleavage is not 100% effective.

FIG. 4B shows how the NmeAIII cleavage site was determined on the bottom 5'-CTCGGC-3' strand.

A DNA (PhiX174) having an NmeAIII site at 1022 and a convenient primer (713-734) (SEQ ID NO:10) was cut with NmeAIII, yielding ends indicated by the arrows (1). The bottom strand (SEQ ID NO:11) serves as the template for dideoxy DNA sequencing extension (2). The primer was annealed and extended through to the NmeAIII cleavage site. When the reaction reaches the end of the molecule the Taq polymerase added an extra A base (3) (SEQ ID NOS:12 and 13). Sequencing Profile of NmeAIII cut PhiX174 DNA (ABI377 Sequencer, Applied Biosystems, Inc., Foster City, Calif.) is provided in (4) (SEQ ID NO:14) as described above.

Figures 2, 4C:
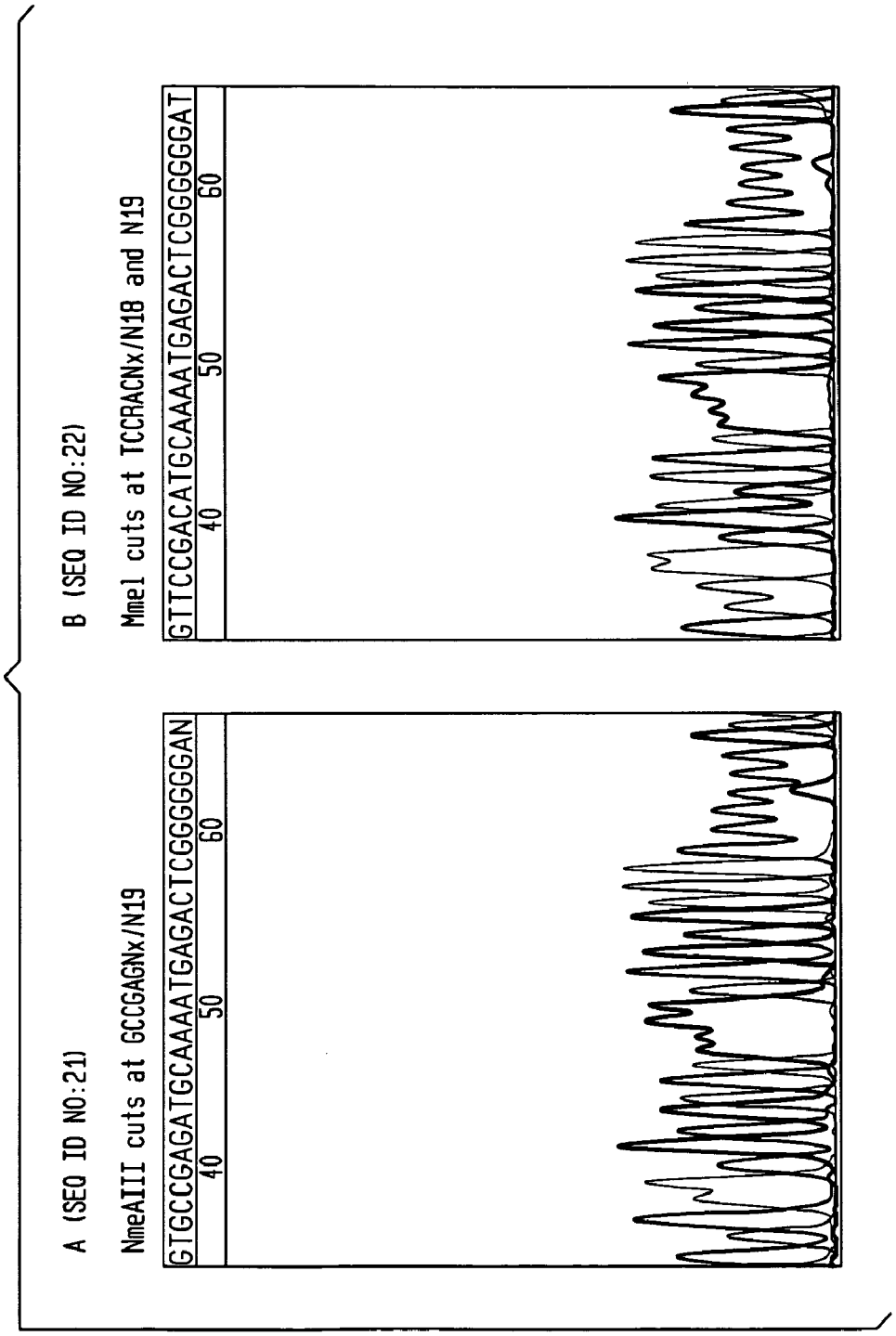

FIGS. 4C-1 and 4C-2 show a comparison of NmeAIII and MmeI cleavage positions for a DNA substrate having the identical sequence of nucleotides in the DNA sequence after the recognition site up to the putative cut site. The results are consistent with FIGS. 4A and 4B. This shows that the difference in cleavage specificity and cleavage distance from the recognition site is independent of the character of the intervening sequence.

An NmeAIII and an MmeI recognition site was cloned into the polylinker of pUC19 DNA adjacent to the same intervening sequence between the position of cutting and recognition. The intervening sequence chosen is the sequence flanking the NmeAIII site at 3426 in PhiX174. The DNA was then cleaved with NmeAIII or MmeI (position of cleavage indicated by the arrows) in (1) (SEQ ID NO:15) and (2)(SEQ ID NO:16).

The primer (NEB1224) was annealed and extended through the NmeAIII site or MmeI site. When the reaction reached the end of the molecule (SEQ ID NOS:17-20), the Taq polymerase added an extra A base. An extra A base was added at the two positions for MmeI, indicating variability in the cleavage position (3) and (4). Sequencing profiles for NmeAIII and MmeI (SEQ ID NOS:21 and 22) were generated showing the cleavage sites for these enzymes.

Figure 5:
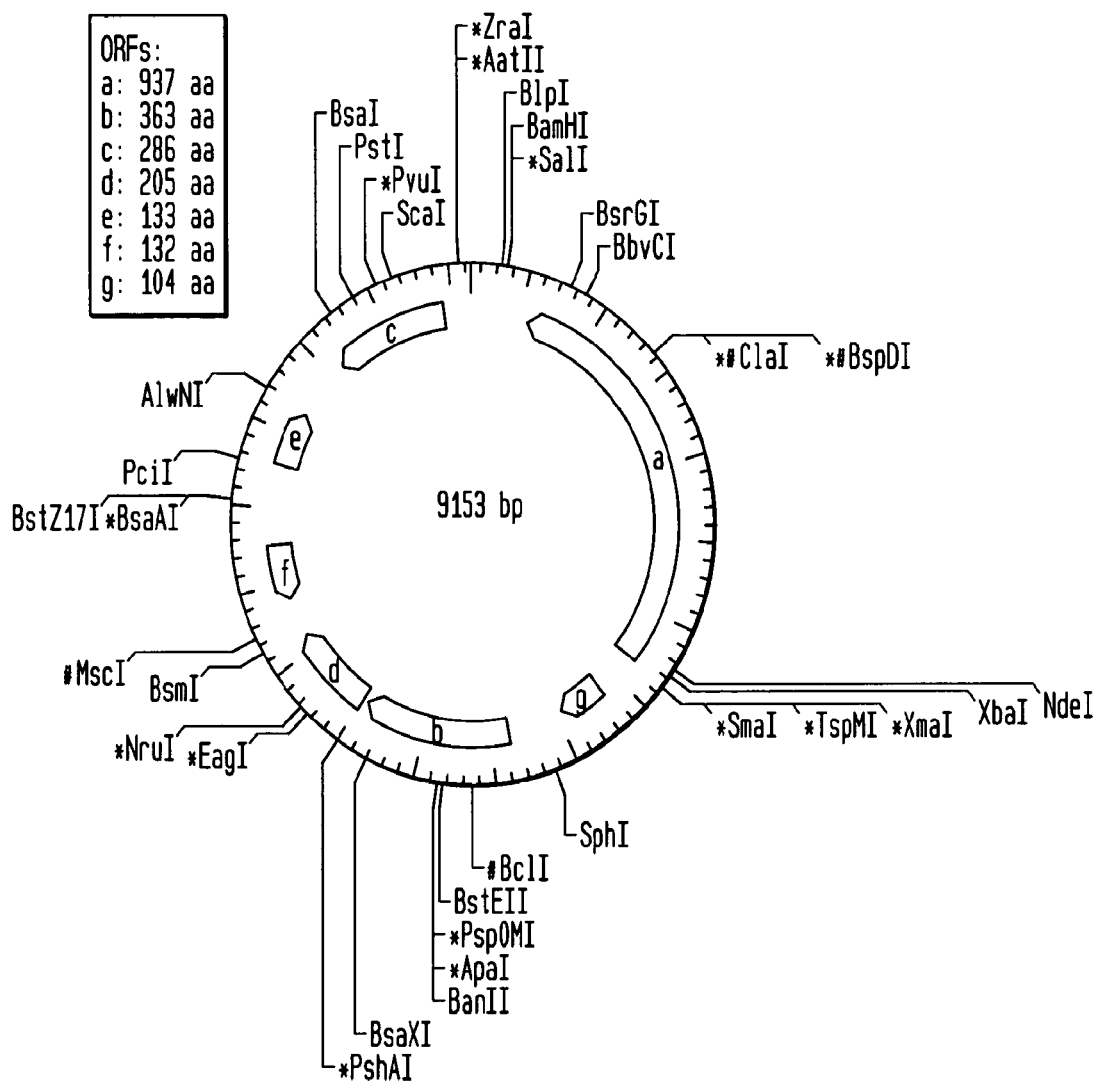

FIG. 5 shows a restriction map for the pAII17-NmeAIII plasmid.

FIGS. 6-1 to 6-2 shows a DNA fragment encoding NmeAIII (2814 bp) (SEQ ID NO:23).

FIG. 7 shows an NmeAIII amino acid sequence (937 amino acids) (SEQ ID NO:24).

FIGS. 8-1 to 8-6 show an NmeAIII-pAII17 construct (SEQ ID NO:25).

DETAILED DESCRIPTION OF THE EMBODIMENTS

Present embodiments of the invention relate to a DNA fragment that codes for a polypeptide possessing site-specific restriction endonuclease and methyltransferase activities. An amino acid sequence of interest from *Neisseria meningitidis* Z2491 was identified because it has significant similarity to the amino acid sequence of MmeI (see for example, U.S. Pat. No. 7,115,407). Genomic DNA was obtained from the *N. meningitidis* strain and the DNA fragment for the putative gene was amplified by PCR and cloned into an expression vector, pRRS, and introduced into *E. coli*. The transformed cells were grown, induced and assayed for restriction endonuclease activity. However, the hypothetical enzyme did not appear to have any detectable endonuclease activity.

It was decided to try to convert the hypothetical enzyme into an active restriction endonuclease.

Further examination of the protein sequence revealed that the NMA1791 hypothetical protein sequence was shorter than the MmeI protein sequence but nevertheless shared significant similarity in the BLAST search starting from near the beginning of the NMA1791 sequence, with residue 13 corresponding to MmeI residue 144, and with further matches throughout the rest of the sequences. It was hypothesized that the observed truncation of the NMA1791 hypothetical protein sequence was the reason for the lack of functional endonuclease activity.

Consequently, the sequence was extended. The reading frame (306 nucleotides) was extended in a 5' direction to the predicted TTG start codon before encountering a stop codon. Even this longer potential reading frame did not extend similarity to the beginning of MmeI sequence, nor was there a plausible putative start codon (ATG, GTG or TTG).

After additional experimentation, it was determined that the extension of the putative open reading frame to a plausible start codon, ATG, located at position 1,733, 738 in the *N. meningitidis* DNA sequence (Genbank Accession No. NC_003116.1) yielded an amino acid sequence with significant similarity to the MmeI amino acid sequence from very near the start of the both sequences. This potential extension of the reading frame for NMA1791, however, contained a stop codon, 5'-TAG-3', at amino acid position 32 of the new reading frame. We cloned and expressed the *N. meningitidis* DNA from this alternative start position to the end of the NMA1791 reading frame (positions 1,733,738 to 1,736,551) and assayed for restriction endonuclease activity. No activity was observed.

The cloned DNA was then sequenced and it was confirmed that the cloned sequence matched the sequence in the database sequence with a TAG stop codon located at position 32 of this identified potential open reading frame.

It was again concluded that this naturally occurring sequence does not express a restriction endonuclease in *N. meningitidis*.

Construction of a Novel Active Endonuclease that Recognizes GCCGAG and a Clone for Expressing the Endonuclease The amino acid sequence from the identified extended potential open reading frame was aligned with the amino acid sequence of MmeI and 19 other sequences that all have highly significant similarity to MmeI (and each other). At the position where the extended potential sequence had a stop codon, TAG, we observed that the homologous sequences encoded a hydrophobic residue: most often a tryptophan, but sometimes a phenylalanine or a leucine or isoleucine. We reasoned that changing the stop codon to a codon for any of phenylalanine, leucine, isoleucine or tryptophan might introduce activity into the inactive enzyme. In Examples 2 and 3, we showed that this approach was effective. The nucleotide codon for tryptophan is TGG, while the observed stop codon at this position in *N. meningitidis* DNA was TAG. By changing the TAG to TGG and expressing the DNA from the ATG codon at position 1,733,738 (GenBank coordinate for *N. meningitidis* Z2491), a polypeptide was obtained that had restriction endonuclease function.

The creation of an active restriction endouclease was practically achieved as follows:
(a) Site-directed mutagenesis was performed using an NEB (Ipswich, Mass.) kit on the expression vector that had the *N. meningitidis* DNA from 1,733,738 to 1,736, 551 to change the A of the TAG stop codon to G, to code for the tryptophan TGG codon.
(b) The altered DNA was then expressed in *E. coli* and a protein extract from the *E. coli* cells assayed for endonuclease activity (Example 1).
(c) From these manipulations, a site-specific endonuclease was obtained (FIG. 2).
(d) We purified this endonuclease and characterized the recognition sequence and position of cleavage relative to the recognition sequence (Examples 2 and 3).

We found that the altered DNA so expressed produced a restriction endonuclease, which we named NmeAIII, which recognizes 5'-GCCGAG-3' in double-stranded DNA and cleaves either 21 and 19 nucleotides, or 20 and 18 nucleotides away from the recognition sequence as indicated: GCCGAGN21/N19 or GCCGAGN20/N18 (see Examples 2 and 3).

In summary, a novel DNA fragment (FIGS. 6-1 and 6-2) or variants is described that encode a novel restriction endonuclease, having the following properties:
(a) recognizes the nucleotide sequence 5'-GCCGAG-3' in a double-stranded DNA molecule as shown below,

```
5'-GCCGAG-3'

3'-CGGCTC-5'
```

(wherein G represents guanine, C represents cytosine, A represents adenine and T represents thymine);
(b) cleaves DNA in the phosphodiester bond following the 21st or 20th nucleotide 3' to the recognition sequence 5'-GCCGAG-3 and preceding the 19th or 18th nucleotide 5' to the complement strand of the recognition sequence 5'-CTCGGC-3' to produce a 2 base 3' extension:

```
5'-GCCGAG(N21)/-3'  or  5'-GCCGAG(N20)/-3'

3'-CGGCTC(N19)/-5'  or  3'-CGGCTC(N18)/-5';
and
```

(c) methylates the recognition sequence specified in (a) in vivo to protect the host DNA from cleavage by the NmeAIII endonuclease activity.

Although a full length sequence for DNA encoding the restriction endonuclease is provided, present embodiments additionally encompass fragments of varying lengths that encode the NmeAIII endonuclease. The amino acid at position 32 of the NmeAIII endonuclease may be preferentially selected from tryptophan, phenylalanine, leucine or isoleucine.

NmeAIII endonuclease fits the category of Type IIE restriction endonucleases in that it seems to require two or more recognition sequences for efficient cleavage, with one site being cleaved and one site acting as an effector (Roberts et al. *Nucl. Acids Res.* 31: 1805-1812 (2005)). The cleavage patterns observed are stable but partial digest DNA fragment banding patterns were observed even with excess enzyme, indicating that the enzyme does not cleave the substrate DNA completely. Addition of excess short oligonucleotides containing the specific DNA recognition sequence can drive the endonuclease cleavage of the DNA to near completion, which is consistent with the Type IIE type of endonuclease.

The ability of NmeAIII to cleave at a predominantly single site at a long reach position from the recognition site has a variety of uses in molecular biology. For example, the 19-21 base pair reach from the recognition site offers a means for making DNA tags that can be used for "Paired Ends" DNA sequencing where sequences from both ends of random clones are determined and assembled into sequence contigs. The sequence data and their linking information can then be used to construct clone maps in the form of scaffolds. This can be effectively performed using paired end ditagging and multiplex sequencing techniques (Ng et al. *Nucleic Acids Res.* 34(12):e84 (2006)). DNA tags can also be used for generating duel end sequence data (sequences generated from each end of a template) in shotgun sequence assembly (Dempsey et al. *J. Bacteriol.* 188(16): 5904-5914 (2006)). In such strategies, a recognition site is embedded in a cloning vector or in an adapter oligonucleotide ligated to the nucleic acid to be interrogated. The longer the distance between the cleavage site and the fixed recognition sequence, the more novel sequence is obtained and thus the more useful the enzyme for such purposes.

All references cited above and below, as well as U.S. provisional application Ser. No. 60/877,265 filed Dec. 27, 2006, are incorporated by reference.

EXAMPLES

Example I

Creating the NmeAIII DNA Fragment and Cloning that Fragment into E. Coli

The NMA1791 reading frame, labeled as a hypothetical protein in Genbank database (NP_284504), was analyzed and found to be incomplete. A potential start codon, ATG, was identified at position 1,733,738 in the N. meningitidis genomic sequence. The identified reading frame starting at this position gave an amino acid sequence that has significant similarity to the known endonucleases throughout the entire sequence. This identified potential start codon was in frame with the NMA1791 incomplete reading frame; however, there was a stop codon, TAG, at amino acid position 32, nucleotide position 1,733,831 to 1,733,833, in N. meningitidis genome sequence that disrupted this reading frame.

The identified, extended reading frame from 1,733,738 to 1,736,551 was cloned and expressed in E. coli to see if this DNA fragment from N. meningitidis would express an endonuclease activity.

Oligonucleotide primers were synthesized to specifically amplify the identified DNA fragment from N. meningitidis Z2491 genomic DNA for expression in a cloning vector such as pRRS (Skoglund, Gene 88: 1-5 (1990)) or pAII17 (U.S. Pat. No. 5,371,006). The forward primer contained a PstI site for cloning, a stop codon in frame with the lacZ gene of the pRRS vector, a consensus E. coli ribosome-binding site, 5'-AGGAGGT-3', an NdeI site at the start of the reading frame for cloning, the ATG start codon, and 21 nucleotides matching the N. meningitidis DNA sequence from position 1,733,738 to 1,733,758:

```
                                       (SEQ ID NO: 26)
5'- GTT CTG GAG TTA AGG AGG TAA CAT ATG AAA ACC

CTG CTC CAA CTC -3'
```

The reverse primer introduced BamHI and SalI sites for cloning and had 23 nucleotides that matched the N. meningitidis Z2491 DNA sequence 3' to the end of the NmeAIII open reading frame at position 1,736,684 to 1,736,662:

```
                                       (SEQ ID NO: 27)
5'-GTT GGA TCC GTC GAG CCT ACG CAA TTG CTT TTG

CGG -3'
```

The NmeAIII gene was amplified in a PCR reaction by combining:
- 40 µl 10× Thermopol buffer (NEB, Ipswich, Mass.)
- 24 µl 4 mM dNTP solution
- 20 µl forward primer (10 mM stock) (SEQ ID NO:26)
- 20 µl reverse primer (10 mM stock) (SEQ ID NO:27)
- 1 µl N. meningitidis Z2491 genomic DNA (200 mg/ml stock)
- 295 µl dH$_2$O
- 3 µl (6 units) Vent® DNA polymerase (NEB, Ipswich, Mass.)

The reaction was mixed and aliquoted into 5 tubes of 80 µl each. MgSO$_4$ was added (100 mM stock) to bring the final concentration of Mg++ ions to 2 mM, 3 mM, 4 mM, 5 mM and 6 mM, respectively. The cycling parameters were 95° C. for 30 seconds, 60° C. for 30 seconds, and 72° C. for 3 minutes, for 25 cycles. The reactions were analyzed by gel electrophoresis. The 3 mM through 6 mM Mg++ reactions were found to contain a DNA band of the desired size of approximately 2.9 kb. These reactions were pooled and the 2.9 kb band was gel purified. The 2.9 kb amplified N. meningitidis DNA fragment was digested with NdeI and BamHI endonucleases (NEB, Ipswich, Mass.) in NEBuffer BamHI (NEB, Ipswich, Mass.) according to the manufacturer's instructions. The small fragments cleaved off the ends of the 2.9 kb DNA fragment were removed, along with the endonucleases, by purification on a Zymo Research "DNA Clean and Concentrate 5" spin column according to the manufacturer's instructions (Zymo Research, Orange, Calif.).

The amplified, cleaved N. meningitidis DNA fragment was ligated to pAII17 vector, previously cleaved with NdeI and BamHI and dephosphorylated, in a 20 ml reaction using NEB T4 DNA ligase according to the manufacturer's instructions (NEB, Ipswich, Mass.). 5 µl of the ligation reaction was transformed into 50 µl chemical competent E. coli ER2566 cells (NEB, Ipswich, Mass.) and the cells were plated on L-broth plates containing 100 µg/ml ampicillin and incubated at 37° C. overnight. Six representatives were analyzed as follows: plasmid from each colony was isolated by miniprep procedures and digested with BamHI and NdeI endonucleases to determine if they contained the correct size insert. 5 of the 6 transformants had the correct size insert of approximately 2900 bp. The five clones were tested to see if they produced endonuclease activity. The clones were grown to mid log phase (klett of 120 to 150) at 37° C. in 30 mL L-broth containing 100 µg/ml ampicillin. The culture was then induced by the addition of IPTG to 0.4 mM and grown for an additional 90 minutes. The cells were harvested by centrifugation, suspended in 1.5 mL sonication buffer (20 mM Tris-HCl, 1 mM DTT, 0.1 mM EDTA, pH7.5) and broken by sonication. The crude lysate was cleared by centrifugation and the supernatant recovered. The lysate was assayed for endonuclease activity by serial dilution of the lysate in 1× reaction buffer NEBuffer 4 (NEB, Ipswich, Mass.) containing 20 µg/ml lambda DNA substrate, or 20 µg/ml pBC4 DNA substrate linearized with NdeI, and supplemented with SAM (S-adenosyl-L-methionine) at 80 µM final concentration. The reactions were incubated for 30 minutes at 37° C. The reaction products were analyzed by agarose gel electrophoresis on a 1% agarose gel in 1×TBE buffer.

None of the clones produced endonuclease activity. The clones were sequenced and the TAG stop codon at position 1,733,831 to 1,733,833 of the N. meningitidis genomic sequence was present, indicating that the sequence in the database was correct; this stop codon was not an artificial sequencing error but was the accurate sequence of the N. meningitidis DNA. The DNA fragment encoding the open reading frame from N. meningitidis DNA, even when extended from the shortened version found in the database (NMA1791) to include all the sequence having similarity to MmeI, did not encode an active endonuclease.

We reasoned that we might be able to create a DNA fragment encoding an endonuclease by changing the TAG stop codon described above to code for an amino acid. The choice of the amino acid to insert at this position was guided by comparison with amino acid sequences of MmeI, CstMI and other sequences identified from sequence databases that have highly significant scores (Expectation value, E, of E less than e-20) in a BLAST search of the database using the extended N. meningitidis open reading frame amino acid sequence. For the comparison twenty sequences were aligned with the extended *N. meningitidis* sequence using ClustalW, (www.e-bi.ac.uk/clustalw) of which 65% of the sequences examined had a tryptophan at the position of the *N. meningitidis* stop codon, 15% had a phenylalanine, 10% had a leucine, 5% an isoleucine, and 5% had a cysteine. All except the cysteine are hydrophobic residues. We chose to replace the stop codon with sequence coding for tryptophan, although it is likely we could use phenylalanine, leucine or isoleucine at this position, and possibly cysteine as well. To create the changed DNA sequence we employed the Phusion Site-Directed Mutagenesis Kit (NEB, Ipswich, Mass.). Two primers were synthesized, one of which had TGG in place of TAG at the position of the *N. meningitidis* stop codon, and used the primers according to the manufacturer's directions for the mutagenesis (FIG. 1). The sequence of the forward primer was: 5'-pTGGAACGAATTTTTCGCCATTTTC-3' (SEQ ID NO:28) where p indicates a phosphate group. The second base, "G" (underlined) differs from the *N. meningitidis* sequence "A" at this position. The reverse primer was: 5'-pGAAGGTGTCTTTCTCGCG-3' (SEQ ID NO:29). One of the pAII17 clones carrying the *N. meningitidis* DNA fragment from 1,733,738 to 1,736,684 was employed as the template for PCR amplification with these primers in a reaction consisting of:

0 μl 5× Phusion HF buffer
1 μl pAII17-*N. meningitidis* plasmid
15 μl forward mutagenic primer (SEQ ID NO:28)
15 μl reverse primer (SEQ ID NO:29)
7.5 μl dNTPs (10 mM stock)
202 μl dH$_2$O
3 μl (6 units) Phusion DNA polymerase
Amplification Conditions Were:
98° C. for 1 minute for one cycle, then 25 cycles of 98° C. for 10 seconds, 63° C. for 20 seconds, and 72° C. for 4 minutes. The amplified DNA was purified on a Zymo Research (Orange, Calif.) Spin column according to the manufacturer's instructions and eluted in 20 μl TE. 3 μl of the DNA was ligated in a 20 μl reaction with T4 DNA ligase (NEB, Ipswich, Mass.). 4 μl of the ligation reaction was transformed into 50 μl chemical competent ER2566 cells (NEB, Ipswich, Mass.) and plated on LB plates containing 100 micrograms/mL ampicillin.

Two individual transformants were grown to express the altered DNA fragment to test for endonuclease activity. A colony was inoculated into 60 mL LB containing 100 micrograms per ml ampicillin in a 250 ml flask and grown to mid log phase at 37° C. with shaking. At mid log, the cells were induced to express protein from the DNA fragment by addition of IPTG to 0.4 mM final concentration and grown for an additional 2 hours. The cells were then harvested by centrifugation, resuspended in 3 ml sonication buffer and lysed by sonication. The crude cell extract was clarified by centrifugation and tested for endonuclease activity by serial dilution of the lysate in 1× reaction buffer NEBuffer 4 (NEB, Ipswich, Mass.) supplemented with SAM (S-adenosyl-L-methionine) at 80 μM final concentration and either 20 μg/ml lambda DNA substrate, or 20 μg/ml pBC4 DNA substrate linearized with NdeI. The reactions were incubated for 30 minutes at 37° C. The reaction products were analyzed by agarose gel electrophoresis on a 1% agarose gel in 1×TBE buffer. Both transformants tested expressed a specific endonuclease (FIG. 1).

Example II

Determination of the NmeAIII Specific DNA Recognition Sequence

The NmeAIII endonuclease was purified from the crude cell extract on a 1 ml Heparin HiTrap column (Pharmacia, Piscataway, N.J.). The crude extract was diluted to 10 ml in buffer A (20 mM Tris pH7.5, 1 mM DTT, 0.1 mM EDTA) containing 50 mM NaCl and applied to the column previously washed and equilibrated in buffer A containing 50 mM NaCl. A 40-milliliter linear gradient from 50 mM to 1M NaCl in buffer A was applied to the column and 1 ml fractions were collected. The fractions were assayed for endonuclease activity. The NmeAIII endonuclease activity eluted at approximately 0.35M NaCl.

The purified NmeAIII from the heparin column was used to digest pUC19, pBR322, PhiX174 and pBC4 DNAs in order to map the locations of NmeAIII cutting in these DNAs. NmeAIII cutting was mapped to approximate positions of 70, 1125 and 3530 in pBR322 DNA, to approximate positions of 1050, 3440 and 4740 in PhiX174 DNA, and to approximate positions of 1900, 3715, 4990, 5385, 6995 and 9750 in pBC4 (FIG. 3). The distance between positions of cutting was entered into the REBPredictor program as fragment sizes for pBR322 DNA (http://tools.neb.com/REBpredictor/index.php). The fragment sizes entered were 2405, with a 4% error margin, 1050 with 6% margin and 900 with 10% error margin. A number of possible recognition sequences were returned, and these were examined to see where they occur in pBR322 and the other DNAs mapped for NmeAIII. One of the potential recognition sequences predicted by REBPredictor, 5'-GCCGAG-3', correlated with the position of NmeAIII cutting.

We found that the sequence 5'-GCCGAG-3' occurs in pBR322 at positions 116, 1168 and 3489, with the 116 and 1168 positions oriented to cleave the DNA 5' to the site (at a smaller position number than the recognition sequence by approximately 20 nucleotides, i.e. at approximately positions 96 and 1148), while the 3489 site is oriented to cleave the DNA 3' to the recognition site (i.e., at a position approximately 25 nucleotides greater than the position number of the recognition site, or 3514 in this case). These 5'-GCCGAG-3' positions agree with the observed positions cut by the endonuclease. The 5'-GCCGAG-3' sequence positions in PhiX174 and pBC4 agree with the experimentally observed positions of cleavage, from which we determine that NmeAIII endonuclease recognizes the sequence 5'-GCCGAG-3' in double stranded DNA.

Example III

Determination of the NmeAIII Cleavage Site

The position of the NmeAIII DNA cleavage site relative to the recognition sequence was determined by cleaving a suitable DNA molecule and then performing DNA sequencing from a suitable primer to the end of the cleaved DNA template. Multiple NmeAIII cut sites were tested because we observed some small variation in the exact distance from the recognition sequence to the position of cleavage, which we believe is due to the nature of the DNA sequence occurring between any given recognition site and cutting positions. Several DNAs (PhiX174, pBC4, pUC19 and pBR322) were employed as the templates. These templates were chosen because they have more than three NmeAIII recognition sites to test and primers available to sequence through these sites. The templates were cleaved with NmeAIII by combining:

25 μl 10× NEBuffer #4 (NEB, Ipswich, Mass.)
5 μl PhiX174 DNA (5 μg)
2.5 μl BSA
218 μl dH$_2$O
0.6 μl SAM (32 mM stock)
2 μl NmeAIII (20 units)

and incubating for 15 minutes at 25° C. The cleaved DNA was purified and concentrated using a Qiagen QiaPrep DNA spin column according to the manufacturer's instructions (Qiagen, Valencia, Calif.). The DNA was eluted in a volume of 50 μl (FIG. 3)

Sequencing Reactions

The sequencing reactions were performed using an ABI377 DNA sequencer according to the manufacturer's instructions, using cleaved template DNAs (PhiX174 or pBC4) and one of several primers:

```
P344-350:
5'-TGATAGGGTCTTTTACCAGCACT-3'        (SEQ ID NO: 30)

P344-351:
5'-TAATGGCGTCGAGCGTCCGGTT-3'         (SEQ ID NO: 31)

NEB1224:
5'-CGCCAGGGTTTTCCCAGTCACGAC-3'       (SEQ ID NO: 32)
```

The results indicate NmeAIII cleaves DNA at a significant distance from the recognition sequence, either between the 21st and the 22nd nucleotides 3' to the recognition sequence in the 5'-GCCGAG-3 strand of the DNA, and between the 19th and 20th nucleotides 5' to the recognition sequence in the complement stand, 5'-CTCGGC-3', or one base closer to the recognition sequence, to produce a 2 base 3' extension (FIGS. 4A and 4B). The position of cleavage observed varied somewhat between two positions, largely between the 21st and 22nd nucleotides 3' to the recognition sequence in the top strand, 5'-GCCGAG-3', but sometimes between the 20th and 21st nucleotides. Likewise, there was some variation in the bottom strand cutting position, largely between the 19th and 20th nucleotides 5' to the recognition sequence in the complement stand, 5'-CTCGGC-3', or one base closer to the recognition sequence between the 18th and 19th nucleotides 5' to the recognition sequence in the complement stand, 5'-CTCGGC-3'.

Because NmeAIII cut at a large distance from the DNA sequence that is recognized and specifically bound by the enzyme, it may be that the particular DNA sequence between the recognition sequence and the position of cutting affects whether the cut position is 21/19 or 20/18 nucleotides away from the recognition sequence. This theory was tested and compared with results for MmeI, which previous to NmeAIII had the longest distance of cutting away from the recognition site of any known type II endonuclease.

A DNA was constructed having either the MmeI recognition site, 5'-TCCRAC-3', or the NmeAIII recognition site, 5'-GCCGAG-3', followed by the same DNA sequence, from Phi174 in which we observed NmeAIII cutting at 21/19 nucleotides from the recognition site at 3426. The MmeI construct was cut and sequenced with MmeI as above, and the NmeAIII construct was similarly tested. The results showed that NmeAIII cuts this construct predominantly at 21/19 bases from the recognition site, while MmeI produces a mixture of 21/19 and 20/18 away from its recognition site (FIGS. 4C-1 and 4C-2). These results showed that NmeAIII has a slightly longer reach than MmeI, though not by a whole nucleotide. NmeAIII will thus be more likely to cut one base farther from its recognition sequence than will MmeI. However, for some intervening sequences between the recognition sites and cut positions, these enzymes will cleave at the same distance, and for others NmeAIII will cleave one base farther than MmeI.

NmeAIII Characteristics:

The NmeAIII endonuclease was assayed in NEBuffer 1, NEBuffer 2, NEBuffer 3 and NEBuffer 4, all supplemented with BSA to 100 micrograms/ml and SAM at 80 micromolar final concentration. NmeAIII was most active in NEBuffer 4, with NEBuffer 1 yielding approximately 10% of the activity observed in NEBuffer 4, and NEBuffer 2 and NEBuffer 3 yielding less than 5% activity (NEB, Ipswich, Mass.).

What is claimed is:

1. An isolated protein, comprising: an amino acid sequence which is at least 90% sequence identical to SEQ ID NO: 24, the amino acid sequence comprising, at a position corresponding to position 32 of SEQ ID NO: 24, an amino acid residue selected from the group consisting of tryptophan, phenylalanine, leucine, and cysteine, wherein said isolated protein (i) has endonuclease activity, (ii) recognizes a sequence consisting of 5'-GCCGAG-3' within a double-stranded DNA substrate, and (iii) cleaves said double-stranded DNA substrate predominantly at 19 nucleotides on one strand and 21 nucleotides on the complementary strand from the recognition site.

2. The protein of claim 1, comprising the amino acid sequence of SEQ ID NO:24.

3. The protein of claim 1, comprising the amino acid sequence of SEQ ID NO:24, except that at a position corresponding to position 32 of SEQ ID NO:24, the amino acid residue is selected from the group consisting of tryptophan, phenylalanine, leucine, and cysteine.

4. A kit comprising an isolated protein that has an amino acid sequence which is at least 90% sequence identical to SEQ ID NO: 24, the amino acid sequence comprising, at a position corresponding to position 32 of SEQ ID NO: 24, an amino acid residue selected from the group consisting of tryptophan, phenylalanine, leucine, and cysteine, wherein said isolated protein (i) has endonuclease activity, (ii) recognizes a sequence consisting of 5'-GCCGAG-3' within a double-stranded DNA substrate, and (iii) cleaves said double-stranded DNA substrate predominantly at 19 nucleotides on one strand and 21 nucleotides on the complementary strand from the recognition site.

5. A method comprising the steps of:
(a) creating a DNA tag by cleaving a target DNA with an isolated protein comprising an amino acid sequence which is at least 90% sequence identical to SEQ ID NO: 24, the amino acid sequence comprising, at a position corresponding to position 32 of SEQ ID NO: 24, an amino acid residue selected from the group consisting of tryptophan, phenylalanine, leucine, and cysteine, wherein said isolated protein (i) has endonuclease activity, (ii) recognizes a sequence consisting of 5'-GCCGAG-3' within a double-stranded DNA substrate, and (iii) cleaves said double-stranded DNA substrate predominantly at 19 nucleotides on one strand and 21 nucleotides on the complementary strand from the recognition site; and
(b) using the DNA tag as a unique identifier for paired end sequencing of DNA or serial analysis of gene expression.

* * * * *

SEQUENCE LISTING

<160> NUMBER OF SEQ ID NOS: 32

<210> SEQ ID NO 1
<211> LENGTH: 79
<212> TYPE: DNA
<213> ORGANISM: Neisseria meningitidis

<400> SEQUENCE: 1
gaccaaaccg acgaactccg cgagaaagac accttctaga acgaattttt cgccattttc    60
ggcatcgacc gcaaaaacg                                                 79

<210> SEQ ID NO 2
<211> LENGTH: 25
<212> TYPE: PRT
<213> ORGANISM: Neisseria meningitidis

<400> SEQUENCE: 2

Asp Gln Thr Asp Glu Arg Arg Glu Lys Asp Thr Phe Asn Glu Phe Phe
1               5                   10                  15

Ala Ile Phe Gly Ile Asp Arg Lys Asn
            20                  25

<210> SEQ ID NO 3
<211> LENGTH: 24
<212> TYPE: DNA

```
<213> ORGANISM: artificial
<220> FEATURE:
<223> OTHER INFORMATION: primer

<400> SEQUENCE: 3
tggaacgaat ttttcgccat tttc                                          24

<210> SEQ ID NO 4
<211> LENGTH: 18
<212> TYPE: DNA
<213> ORGANISM: artificial
<220> FEATURE:
<223> OTHER INFORMATION: primer

<400> SEQUENCE: 4
gaaggtgtct ttctcgcg                                                 18

<210> SEQ ID NO 5
<211> LENGTH: 45
<212> TYPE: DNA
<213> ORGANISM: artificial
<220> FEATURE:
<223> OTHER INFORMATION: primer

<400> SEQUENCE: 5
gtcagcgggg tctggtgtgg gaggacgatg actcggcaga cgaca                   45

<210> SEQ ID NO 6
<211> LENGTH: 45
<212> TYPE: DNA
<213> ORGANISM: artificial
<220> FEATURE:
<223> OTHER INFORMATION: primer

<400> SEQUENCE: 6
tgtcgtctgc cgagtcatcg tcctcccaca ccagaccccg ctgac                   45

<210> SEQ ID NO 7
<211> LENGTH: 11
<212> TYPE: DNA
<213> ORGANISM: artificial
<220> FEATURE:
<223> OTHER INFORMATION: primer

<400> SEQUENCE: 7
gtcagcgggg a                                                        11

<210> SEQ ID NO 8
<211> LENGTH: 41
<212> TYPE: DNA
<213> ORGANISM: artificial
<220> FEATURE:
<223> OTHER INFORMATION: complementary strand of seq id no. 5 absent the
      first 4 nucleotides at the 5' end

<400> SEQUENCE: 8
gtctgccgag tcatcgtcct cccacaccag accccgctga c                       41

<210> SEQ ID NO 9
<211> LENGTH: 45
<212> TYPE: DNA
<213> ORGANISM: artificial
<220> FEATURE:
<223> OTHER INFORMATION: determination of cleavage site in the DNA
      strand corresponding to seq id no 5
<220> FEATURE:
<221> NAME/KEY: misc_feature
<222> LOCATION: (11)..(11)
```

```
<223> OTHER INFORMATION: n is a, c, g, or t

<400> SEQUENCE: 9
gtcagcgggg nctggtgtgg gaggacgatg actcggcaga cgaca          45

<210> SEQ ID NO 10
<211> LENGTH: 45
<212> TYPE: DNA
<213> ORGANISM: artificial
<220> FEATURE:
<223> OTHER INFORMATION: primer

<400> SEQUENCE: 10
aaactggcgc cgagcgtatg ccgcatgacc tttcccatct tggct          45

<210> SEQ ID NO 11
<211> LENGTH: 33
<212> TYPE: DNA
<213> ORGANISM: artificial
<220> FEATURE:
<223> OTHER INFORMATION: phage 174 DNA fragment containing NmeAIII
      recognition site

<400> SEQUENCE: 11
aaaggtcatg cggcatacgc tcggcgccag ttt                       33

<210> SEQ ID NO 12
<211> LENGTH: 34
<212> TYPE: DNA
<213> ORGANISM: artificial
<220> FEATURE:
<223> OTHER INFORMATION: complementary strand to seq id no 10 cut by
      NmeAIII

<400> SEQUENCE: 12
aaactggcgc cgagcgtatg ccgcatgacc ttta                      34

<210> SEQ ID NO 13
<211> LENGTH: 33
<212> TYPE: DNA
<213> ORGANISM: artificial
<220> FEATURE:
<223> OTHER INFORMATION: primer extended to the NmeAIII cleavage site
      with insertion of an A by a polymerase at the cleavage site

<400> SEQUENCE: 13
aaaggtcatg cggcatacgc tcggcgccag ttt                       33

<210> SEQ ID NO 14
<211> LENGTH: 44
<212> TYPE: DNA
<213> ORGANISM: artificial
<220> FEATURE:
<223> OTHER INFORMATION: complement to sequence in seq id no 12 minus
      the added A
<220> FEATURE:
<221> NAME/KEY: misc_feature
<222> LOCATION: (33)..(33)
<223> OTHER INFORMATION: n is a, c, g, or t

<400> SEQUENCE: 14
aaactggcgc cgaggtatgc cgcatgacct ttnccatctt ggct           44

<210> SEQ ID NO 15
<211> LENGTH: 33
<212> TYPE: DNA
<213> ORGANISM: artificial
<220> FEATURE:
```

```
<223> OTHER INFORMATION: sequence profile to determine cleavage profile

<400> SEQUENCE: 15
gtgccgagat gcaaaatgag actcgggggg atc                                    33

<210> SEQ ID NO 16
<211> LENGTH: 33
<212> TYPE: DNA
<213> ORGANISM: artificial
<220> FEATURE:
<223> OTHER INFORMATION: primer

<400> SEQUENCE: 16
gttccgacat gcaaaatgag actcgggggg atc                                    33

<210> SEQ ID NO 17
<211> LENGTH: 28
<212> TYPE: DNA
<213> ORGANISM: artificial
<220> FEATURE:
<223> OTHER INFORMATION: primer

<400> SEQUENCE: 17
gtgccgagat gcaaaatgag actcggga                                          28

<210> SEQ ID NO 18
<211> LENGTH: 33
<212> TYPE: DNA
<213> ORGANISM: artificial
<220> FEATURE:
<223> OTHER INFORMATION: primer

<400> SEQUENCE: 18 gatcccccg agtctcattt tgcatctcgg cac                                     33

<210> SEQ ID NO 19
<211> LENGTH: 28
<212> TYPE: DNA
<213> ORGANISM: artificial
<220> FEATURE:
<223> OTHER INFORMATION: primer

<400> SEQUENCE: 19
gttccgacat gcaaaatgag actcggaa                                          28

<210> SEQ ID NO 20
<211> LENGTH: 33
<212> TYPE: DNA
<213> ORGANISM: artificial
<220> FEATURE:
<223> OTHER INFORMATION: primer

<400> SEQUENCE: 20 gatcccccg agtctcattt tgcatgtcgg aac                                     33

<210> SEQ ID NO 21
<211> LENGTH: 32
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (32)..(32)
<223> OTHER INFORMATION: n is a, c, g, or t

<400> SEQUENCE: 21
```

-continued

```
gtgccgagat gcaaaatgag actcggggggg an                             32
```

<210> SEQ ID NO 22
<211> LENGTH: 32
<212> TYPE: DNA
<213> ORGANISM: artificial
<220> FEATURE:
<223> OTHER INFORMATION: primer

<400> SEQUENCE: 22

```
gttccgacat gcaaaatgag actcggggggg at                             32
```

<210> SEQ ID NO 23
<211> LENGTH: 2814
<212> TYPE: DNA
<213> ORGANISM: Neisseria meningitidis

<400> SEQUENCE: 23

```
atgaaaaccc tgctccaact ccaaaccgcc gcacaaaact tcgccgccta ctacaaagac    60
caaaccgacg aacgccgcga aaagacacc ttctggaacg aattttttcgc cattttcggc   120
atcgaccgca aaaacgtcgc ccacttcgaa taccccgtca agaccctgc cgacaacacc    180
caattcgtcg atatattttg ggaaggcatc ttccttgccg aacacaaatc cgccaacaaa   240
aacctgacca aggccaaaga gcaggcgaaa cgttatttac aggaaatcgg cgcaccaag    300
ccctccgcgc tgcccgaata ttacgccgtc agcgattttg cccatttcca cctttaccgc   360
cgcgtacctg aagaaggcgc agaaaaccaa tggcagttcc ctttggaaga attgcctgaa   420
tacatcacgc gcggcgtttt cgacttcatg ttcggcatcg aagccaaagt ccgccaaatt   480
caagaagaag ccaacattca agcggcggcg accatcggca ggctgcacga cgcgctcaaa   540
gaagaaggca tttacgaaga cacgagctg cgcctcttca tcacgcgcct gcttttcctc   600
tttttttgccg acgacagcgc cgttttccgg cgcaactacc ttttccaaga cttttttagaa   660
aactgcaaag aagccgacac gctcggcgac aagctcaatc aactctttga atttctcaac   720
acacccgacc aaaagcgcag caagacccaa agcgaaaaat ttaaaggttt cgaatacgtc   780
aacggcggtc ttttcaaaga acgcctgcgc actttcgact tcactgccaa gcagcaccgc   840
gccttaatcg actgcggcaa ttttgactgg cgcaacatca gtccagaaat cttcggcacg   900
ctcttccaat ccgtcatgga cgcgcaagag cggcgcgaag cgggcgcgca ctacaccgaa   960
gccgccaata tcgacaaagt catcaacggc ctttttttag aaaacctgcg tgccgaattt  1020
gaagccgtca agcccctcaa acgcgacaaa gccaaaaaac tcgccgcctt ctaccaaaaa  1080
atccaaaacc tgcaattcct cgaccctgcc tgcggctgcg gcaacttcct tatcgtcgcc  1140
tacgaccgca tccgcgccct tgaagacgac atcatcgccg aagcccctcaa agacaaagca  1200
gacggcctgt tcgacagccc gtccgtccaa tgccgtctga acagtttca cggcatcgaa  1260
atagacgaat tgccgtcct catcgcccgc accgccatgt ggctcaaaaa ccaccaatgc  1320
aacatccgca cacaaatccg cttcgacggc gaagtcgcct gccatacgct gccgctcgaa  1380
gacgccgccg aaatcatcca cgccaacagc ctccgcacac cttggcaggc ggcggactac  1440
atcttcggca atcccccctt tatcggctcg acctaccaaa ccaaagagca gaaaaacgac  1500
ctcgaaagca tctgcggcca tatcaaaggc tacggcctgt tggattacgt ctgcaactgg  1560
tacgtcaaag ccgcaggcat catggcgcag catccccaag ttcagacggc atttgttttcc  1620
accaattcca tctgccaagg ccagcaggtc gaaatcctct ggggcagcct tttaaaccaa  1680
ggcatcgaaa tccactttgc ccaccgcacc ttccaatgga cgagccaagc cgcaggcaaa  1740
```

-continued

```
gccgccgtcc actgcatcat cgtcggcttc cgccaaaagc cgccaatgcc gtctgaaaaa    1800
accctctacg actatcccga catcaaaggc gaacccgaaa acacgccgt agccaacatc     1860 aatccttatc tgatcgatgc gcccgatttg attatcgcca agcgcagccg tcccatacat    1920
tgcgaacctg atatggtcaa cggaagcaaa ccgaccgaag cggcaaccct tatccttca    1980 accgccgaaa aagatgccct gattgccgcc gaacccttgg cggagcaata catccgcccc   2040
tttatcggcg cggatgagtt tctcaacggc aaaacccgtt ggtgcctgtg gtttcacggc    2100
gtatccgatg tcaaacgcaa ccacgacctg aaacaaatgc cccaagttca gcccgtatt    2160 caggcggtca aaccatgcg cgaagccagc agcgacaaac aaactcaaaa agatgcagca    2220
accccgtggc tttttcaaaa aatccgccag ccttcagacg gcaattatct gattattccg    2280
agcgtgtcgt ctgaaagccg ccgtttcatc cccatcggtt atctgtcgtt tgaaacagtt    2340
gtcagcaatc tggcatttat ccttccaaac gccaccctct accacttcgg catcctcagc    2400
tccaccatgc acaacgcctt tatgcgtacc gttgcaggtc gtctgaaaag cgattatcgc    2460
tactctaata ccgtcgtgta caacaacttc cccttccccg aaagctgccg gttgccgtct    2520
gaaaacgacc gccccgaccc gctccgcgcc gccgtcgaag ccgccgccca accgtcctc    2580 gacgcgcgcg gacaataccg ccgagaagcg caggaagccg gtttgcccga ccgacccctc    2640
gccgaactct atgcgcccga cgcaggctat accgccctcg acaaagccca cgccacccctc   2700 gacaaggcag tcgataaagc ctacggctac aaaacaggca aaataccga cgacgaggca    2760 gaacgcgtcg ccttcctgtt cgagctgtac cgcaaggcgg cggcaattgc gtag          2814
```

<210> SEQ ID NO 24
<211> LENGTH: 937
<212> TYPE: PRT
<213> ORGANISM: Neisseria meningitidis

<400> SEQUENCE: 24

```
Met Lys Thr Leu Leu Gln Leu Gln Thr Ala Ala Gln Asn Phe Ala Ala
1               5                   10                  15

Tyr Tyr Lys Asp Gln Thr Asp Glu Arg Arg Glu Lys Asp Thr Phe Trp
            20                  25                  30

Asn Glu Phe Phe Ala Ile Phe Gly Ile Asp Arg Lys Asn Val Ala His
        35                  40                  45

Phe Glu Tyr Pro Val Lys Asp Pro Ala Asp Asn Thr Gln Phe Val Asp
    50                  55                  60

Ile Phe Trp Glu Gly Ile Phe Leu Ala Glu His Lys Ser Ala Asn Lys
65                  70                  75                  80

Asn Leu Thr Lys Ala Lys Glu Gln Ala Glu Arg Tyr Leu Gln Glu Ile
                85                  90                  95

Gly Arg Thr Lys Pro Ser Ala Leu Pro Glu Tyr Tyr Ala Val Ser Asp
            100                 105                 110

Phe Ala His Phe His Leu Tyr Arg Arg Val Pro Glu Glu Gly Ala Glu
        115                 120                 125

Asn Gln Trp Gln Phe Pro Leu Glu Glu Leu Pro Glu Tyr Ile Thr Arg
    130                 135                 140

Gly Val Phe Asp Phe Met Phe Gly Ile Glu Ala Lys Val Arg Gln Ile
145                 150                 155                 160

Gln Glu Glu Ala Asn Ile Gln Ala Ala Thr Ile Gly Arg Leu His
                165                 170                 175

Asp Ala Leu Lys Glu Glu Gly Ile Tyr Glu Glu His Glu Leu Arg Leu
            180                 185                 190
```

-continued

```
Phe Ile Thr Arg Leu Leu Phe Leu Phe Phe Ala Asp Asp Ser Ala Val
        195                 200                 205

Phe Arg Arg Asn Tyr Leu Phe Gln Asp Phe Leu Glu Asn Cys Lys Glu
210                 215                 220

Ala Asp Thr Leu Gly Asp Lys Leu Asn Gln Leu Phe Glu Phe Leu Asn
225                 230                 235                 240

Thr Pro Asp Gln Lys Arg Ser Lys Thr Gln Ser Glu Lys Phe Lys Gly
                245                 250                 255

Phe Glu Tyr Val Asn Gly Gly Leu Phe Lys Glu Arg Leu Arg Thr Phe
                260                 265                 270

Asp Phe Thr Ala Lys Gln His Arg Ala Leu Ile Asp Cys Gly Asn Phe
            275                 280                 285

Asp Trp Arg Asn Ile Ser Pro Glu Ile Phe Gly Thr Leu Phe Gln Ser
        290                 295                 300

Val Met Asp Ala Gln Glu Arg Glu Ala Gly Ala His Tyr Thr Glu
305                 310                 315                 320

Ala Ala Asn Ile Asp Lys Val Ile Asn Gly Leu Phe Leu Glu Asn Leu
                325                 330                 335

Arg Ala Glu Phe Glu Ala Val Lys Ala Leu Lys Arg Asp Lys Ala Lys
            340                 345                 350

Lys Leu Ala Ala Phe Tyr Gln Lys Ile Gln Asn Leu Gln Phe Leu Asp
        355                 360                 365

Pro Ala Cys Gly Cys Gly Asn Phe Leu Ile Val Ala Tyr Asp Arg Ile
    370                 375                 380

Arg Ala Leu Glu Asp Asp Ile Ile Ala Glu Ala Leu Lys Asp Lys Ala
385                 390                 395                 400

Asp Gly Leu Phe Asp Ser Pro Ser Val Gln Cys Arg Leu Lys Gln Phe
                405                 410                 415

His Gly Ile Glu Ile Asp Glu Phe Ala Val Leu Ile Ala Arg Thr Ala
            420                 425                 430

Met Trp Leu Lys Asn His Gln Cys Asn Ile Arg Thr Gln Ile Arg Phe
        435                 440                 445

Asp Gly Glu Val Ala Cys His Thr Leu Pro Leu Glu Asp Ala Ala Glu
450                 455                 460

Ile Ile His Ala Asn Ser Leu Arg Thr Pro Trp Gln Ala Ala Asp Tyr
465                 470                 475                 480

Ile Phe Gly Asn Pro Pro Phe Ile Gly Ser Thr Tyr Gln Thr Lys Glu
                485                 490                 495

Gln Lys Asn Asp Leu Glu Ser Ile Cys Gly His Ile Lys Gly Tyr Gly
            500                 505                 510

Leu Leu Asp Tyr Val Cys Asn Trp Tyr Val Lys Ala Ala Gly Ile Met
        515                 520                 525

Ala Gln His Pro Gln Val Gln Thr Ala Phe Val Ser Thr Asn Ser Ile
    530                 535                 540

Cys Gln Gly Gln Gln Val Glu Ile Leu Trp Gly Ser Leu Leu Asn Gln
545                 550                 555                 560

Gly Ile Glu Ile His Phe Ala His Arg Thr Phe Gln Trp Thr Ser Gln
                565                 570                 575

Ala Ala Gly Lys Ala Ala Val His Cys Ile Ile Val Gly Phe Arg Gln
            580                 585                 590

Lys Pro Pro Met Pro Ser Glu Lys Thr Leu Tyr Asp Tyr Pro Asp Ile
        595                 600                 605

Lys Gly Glu Pro Glu Lys His Ala Val Ala Asn Ile Asn Pro Tyr Leu
    610                 615                 620
```

Ile Asp Ala Pro Asp Leu Ile Ile Ala Lys Arg Ser Arg Pro Ile His
625                 630                 635                 640

Cys Glu Pro Asp Met Val Asn Gly Ser Lys Pro Thr Glu Gly Gly Asn
            645                 650                 655

Leu Ile Leu Ser Thr Ala Glu Lys Asp Ala Leu Ile Ala Ala Glu Pro
        660                 665                 670

Leu Ala Glu Gln Tyr Ile Arg Pro Phe Ile Gly Ala Asp Glu Phe Leu
    675                 680                 685

Asn Gly Lys Thr Arg Trp Cys Leu Trp Phe His Gly Val Ser Asp Val
690                 695                 700

Lys Arg Asn His Asp Leu Lys Gln Met Pro Gln Val Gln Ala Arg Ile
705                 710                 715                 720

Gln Ala Val Lys Thr Met Arg Glu Ala Ser Ser Asp Lys Gln Thr Gln
            725                 730                 735

Lys Asp Ala Ala Thr Pro Trp Leu Phe Gln Lys Ile Arg Gln Pro Ser
        740                 745                 750

Asp Gly Asn Tyr Leu Ile Ile Pro Ser Val Ser Ser Glu Ser Arg Arg
    755                 760                 765

Phe Ile Pro Ile Gly Tyr Leu Ser Phe Glu Thr Val Val Ser Asn Leu
770                 775                 780

Ala Phe Ile Leu Pro Asn Ala Thr Leu Tyr His Phe Gly Ile Leu Ser
785                 790                 795                 800

Ser Thr Met His Asn Ala Phe Met Arg Thr Val Ala Gly Arg Leu Lys
            805                 810                 815

Ser Asp Tyr Arg Tyr Ser Asn Thr Val Val Tyr Asn Asn Phe Pro Phe
        820                 825                 830

Pro Glu Ser Cys Arg Leu Pro Ser Glu Asn Asp Arg Pro Asp Pro Leu
    835                 840                 845

Arg Ala Ala Val Glu Ala Ala Gln Thr Val Leu Asp Ala Arg Gly
850                 855                 860

Gln Tyr Arg Arg Glu Ala Gln Glu Ala Gly Leu Pro Glu Pro Thr Leu
865                 870                 875                 880

Ala Glu Leu Tyr Ala Pro Asp Ala Gly Tyr Thr Ala Leu Asp Lys Ala
            885                 890                 895

His Ala Thr Leu Asp Lys Ala Val Asp Lys Ala Tyr Gly Tyr Lys Thr
        900                 905                 910

Gly Lys Asn Thr Asp Asp Glu Ala Glu Arg Val Ala Phe Leu Phe Glu
    915                 920                 925

Leu Tyr Arg Lys Ala Ala Ala Ile Ala
930                 935

<210> SEQ ID NO 25
<211> LENGTH: 9153
<212> TYPE: DNA
<213> ORGANISM: Neisseria meningitidis

<400> SEQUENCE: 25
agctttaatg cggtagttta tcacagttaa attgctaacg cagtcaggca ccgtgtatga    60
aatctaacaa tgcgctcatc gtcatcctcg gcaccgtcac cctggatgct gtaggcatag   120
gcttggttat gccggtactg ccgggcctct gcgggatat ccggatatag ttcctccttt    180
cagcaaaaaa cccctcaaga cccgtttaga ggccccaagg ggttatgcta gttattgctc   240
agcggtggca gcagccaact cagcttcctt tcgggctttg ttagcagccg gatccgtcga   300
ccctacgcaa ttgcttttgc ggagatgacg gggtttt agg gtgaagatgg tgggagttgg   360

```
tgggagttgg tgggctgaag cccaccctac gcaactatcc tacgcaacta ctacgcaact    420
actacgcaac tactacgcaa ttgccgccgc cttgcggtac agctcgaaca ggaaggcgac    480
gcgttctgcc tcgtcgtcgg tattttttgcc tgttttgtag ccgtaggctt tatcgactgc   540
cttgtcgagg gtggcgtggg cttgtcgag ggcggtatag cctgcgtcgg gcgcatagag    600
ttcggcgagg gtcggctcgg gcaaaccggc ttcctgcgct tctcggcggt attgtccgcg    660
cgcgtcgagg acggtttggg cggcggcttc gacggcggcg cggagcgggt cggggcggtc    720
gttttcagac ggcaaccggc agctttcggg gaaggggaag ttgttgtaca cgacggtatt    780
agagtagcga taatcgcttt tcagacgacc tgcaacggta cgcataaagg cgttgtgcat    840
ggtggagctg aggatgccga agtggtagag ggtggcgttt ggaaggataa atgccagatt    900
gctgacaact gtttcaaacg acagataacc gatggggatg aaacggcggc tttcagacga    960
cacgctcgga ataatcagat aattgccgtc tgaaggctgg cggattttt gaaaaagcca    1020 cggggttgct gcatcttttt gagtttgttt gtcgctgctg gcttcgcgca tggttttgac   1080
cgcctgaata cgggcttgaa cttggggcat ttgtttcagg tcgtggttgc gtttgacatc    1140
ggatacgccg tgaaaccaca ggcaccaacg ggttttgccg ttgagaaact catccgcgcc    1200
gataaagggg cggatgtatt gctccgccaa gggttcggcg gcaatcaggg catctttttc    1260
ggcggttgaa aggataaggt tgccgccttc ggtcggtttg cttccgttga ccatatcagg    1320
ttcgcaatgt atgggacggc tgcgcttggc gataatcaaa tcgggcgcat cgatcagata    1380
aggattgatg ttggctacgg cgtgttttc gggttcgcct ttgatgtcgg atagtcgta    1440 gagggttttt tcagacggca ttggcggctt ttggcggaag ccgacgatga tgcagtggac    1500
ggcggctttg cctgcggctt ggctcgtcca ttggaaggtg cggtgggcaa agtggatttc    1560
gatgccttgg tttaaaaggc tgccccagag gatttcgacc tgctggcctt ggcagatgga    1620
attggtggaa acaaatgccg tctgaacttg gggatgctgc gccatgatgc ctgcggcttt    1680
gacgtaccag ttgcagacgt aatccaacag gccgtagcct ttgatatggc cgcagatgct    1740
ttcgaggtcg tttttctgct ctttggtttg gtaggtcgag ccgataaagg ggggattgcc    1800
gaagatgtag tccgccgcct gccaaggtgt gcggaggctg ttggcgtgga tgatttcggc    1860
ggcgtcttcg agcggcagcg tatggcaggc gacttcgccg tcgaagcgga tttgtgtgcg    1920
gatgttgcat tggtggtttt tgagccacat ggcggtgcgg gcgatgagga cggcaaattc    1980
gtctatttcg atgccgtgaa actgtttcag acggcattgg acggacgggc tgtcgaacag    2040
gccgtctgct ttgtctttga gggcttcggc gatgatgtcg tcttcaaggg cgcggatgcg    2100
gtcgtaggcg acgataagga agttgccgca ccgcaggca gggtcgagga attgcaggtt    2160
ttggattttt tggtagaagg cggcgagttt tttggctttg tcgcgtttga gggctttgac    2220
ggcttcaaat tcggcacgca ggttttctaa aaaaaggccg ttgatgactt tgtcgatatt    2280
ggcggcttcg gtgtagtgcg cgcccgcttc gcgccgctct tgcgcgtcca tgacggattg    2340
gaagagcgtg ccgaagattt ctggactgat gttgcgccag tcgaaattgc cgcagtcgat    2400
taaggcgcgg tgctgcttgg cagtgaagtc gaaagtgcgc aggcgttctt tgaaaagacc    2460
gccgttgacg tattcgaaac ctttaaattt ttcgctttgg gtcttgctgc gcttttggtc    2520
gggtgtgttg agaaattcaa agagttgatt gagcttgtcg ccgagcgtgt cggcttcttt    2580
gcagttttct aaaagtctt ggaaaggta gttgcgccgg aaacggcgc tgtcgtcggc    2640 aaaaagagg aaagcaggc gcgtgatgaa gaggcgcagc tcgtgttctt cgtaaatgcc    2700
ttcttctttg agcgcgtcgt gcagcctgcc gatggtcgcc gccgcttgaa tgttggcttc    2760
```

```
ttcttgaatt tggcggactt tggcttcgat gccgaacatg aagtcgaaaa cgccgcgcgt    2820
gatgtattca ggcaattctt ccaaagggaa ctgccattgg ttttctgcgc cttcttcagg    2880
tacgcggcgg taaaggtgga aatgggcaaa atcgctgacg gcgtaatatt cgggcagcgc    2940
ggagggcttg gtgcgcccga tttcctgtaa ataacgttcc gcctgctctt tggccttggt    3000
caggtttttg ttggcggatt tgtgttcggc aaggaagatg ccttcccaaa atatatcgac    3060
gaattgggtg ttgtcggcag ggtctttgac ggggtattcg aagtgggcga cgttttttgcg   3120 gtcgatgccg aaaatggcga aaaattcgtt ccagaaggtg tctttctcgc ggcgttcgtc    3180
ggtttggtct ttgtagtagg cggcgaagtt ttgtgcggcg gtttggagtt ggagcagggt    3240
tttcatatgt atatctcctt cttaaagtta aacaaaatta tttctagagg ggaattgtta    3300
tccgctcaca attcccctat agtgagtcgt attaatttcg cgggatcgag atccccggga    3360
attaattccg atcccccaatt cctggcagtt tatggcgggc gtcctgcccg ccaccctccg    3420
ggccgttgct tcgcaacgtt caaatccgct cccggcggat tgtcctact caggagagcg    3480 ttcaccgaca aacaacagat aaaacgaaag gcccagtctt tcgactgagc ctttcgtttt    3540
atttgatgcc tggaattaat tcctggcagt ttatggcggg cgtcctgccc gccaccctcc    3600
gggccgttgc ttcgcaacgt tcaaatccgc tcccggcgga tttgtcctac tcaggagagc    3660
gttcaccgac aaacaacaga taaaacgaaa ggcccagtct ttcgactgag cctttcgttt    3720
tatttgatgc ctggaattaa ttcctggcag tttatggcgg gcgtcctgcc gccaccctc    3780 cgggccgttg cttcgcaacg ttcaaatccg ctcccggcgg atttgtccta ctcaggagag    3840
cgttcaccga caaacaacag ataaaacgaa aggcccagtc tttcgactga gcctttcgtt    3900
ttatttgatg cctggaatta attcctggca gtttatggcg ggcgtcctgc cgccaccct    3960 ccgggccgtt gcttcgcaac gttcaaatcc gctcccggcg gatttgtcct actcaggaga    4020
gcgttcaccg acaaacaaca gataaaacga aaggcccagt ctttcgactg agcctttcgt    4080
tttatttgat gcctggaatt gggaattaat tcttgaagac gaaagggcgg catgcaccat    4140
tccttgcggc ggcggtgctc aacggcctca acctactact gggctgcttc ctaatgcagg    4200
agtcgcataa gggagagcgt cgagatccgg gacaccatcg aatggcgcaa aacctttcgc    4260
ggtatggcat gatagcgccc ggaagagagt caattcaggg tggtgaatgt gaaaccagta    4320
acgttatacg atgtcgcaga gtatgccggt gtctcttatc agaccgtttc ccgcgtggtg    4380
aaccaggcca gccacgtttc tgcgaaaacg cgggaaaaag tggaagcggc gatggcggag    4440
ctgaattaca ttcccaaccg cgtggcacaa caactggcgg caaacagtc gttgctgatt     4500 ggcgttgcca cctccagtct ggccctgcac gcgccgtcgc aaattgtcgc ggcgattaaa    4560
tctcgcgccg atcaactggg tgccagcgtg gtggtgtcga tggtagaacg aagcggcgtc    4620
gaagcctgta aagcggcggt gcacaatctt ctcgcgcaac gcgtcagtgg gctgatcatt    4680
aactatccgc tggatgacca ggatgccatt gctgtggaag ctgcctgcac taatgttccg    4740
gcgttatttc ttgatgtctc tgaccagaca cccatcaaca gtattatttt ctcccatgaa    4800
gacggtacgc gactgggcgt ggagcatctg gtcgcattgg gtcaccagca atcgcgctg    4860 ttagcgggcc cattaagttc tgtctcggcg cgtctgcgtc tggctggctg gcataaatat    4920
ctcactcgca atcaaattca gccgatagcg gaacgggaag gcgactggag tgccatgtcc    4980
ggttttcaac aaaccatgca aatgctgaat gagggcatcg ttcccactgc gatgctggtt    5040
gccaacgatc agatggcgct gggcgcaatg cgcgccatta ccgagtccgg gctgcgcgtt    5100
ggtgcggata tctcggtagt gggatacgac gataccgaag acagctcatg ttatatcccg    5160
```

```
ccgtcaacca ccatcaaaca ggattttcgc ctgctggggc aaaccagcgt ggaccgcttg    5220
ctgcaactct ctcagggcca ggcggtgaag ggcaatcagc tgttgcccgt ctcactggtg    5280
aaaagaaaaa ccaccctggc gcccaatacg caaaccgcct ctccccgcgc gttggccgat    5340
tcattaatgc agctggcacg acaggtttcc cgactggaaa gcgggcagtg agcgcaacgc    5400
aattaatgtg agttagctca ctcattaggc cgggatctcg accgatgccc ttgagagcct    5460
tcaacccagt cagctccttc cggtgggcgc ggggcatgac tatcgtcgcc gcacttatga    5520
ctgtcttctt tatcatgcaa ctcgtaggac aggtgccggc agcgctctgg gtcattttcg    5580
gcgaggaccg ctttcgctgg agcgcgacga tgatcggcct gtcgcttgcg gtattcggaa    5640
tcttgcacgc cctcgctcaa gccttcgtca ctggtcccgc caccaaacgt ttcggcgaga    5700
agcaggccat tatcgccggc atggcggccg acgcgctggg ctacgtcttg ctggcgttcg    5760
cgacgcgagg ctggatggcc ttccccatta tgattcttct cgcttccggc ggcatcggga    5820
tgcccgcgtt gcaggccatg ctgtccaggc aggtagatga cgaccatcag ggacagcttc    5880
aaggatcgct cgcggctctt accagcctaa cttcgatcac tggaccgctg atcgtcacgg    5940
cgatttatgc cgcctcggcg agcacatgga acgggttggc atggattgta ggcgccgccc    6000
tataccttgt ctgcctcccc gcgttgcgtc gcggtgcatg gagccgggcc acctcgacct    6060
gaatggaagc cggcggcacc tcgctaacgg attcaccact ccaagaattg gagccaatca    6120
attcttgcgg agaactgtga atgcgcaaac caacccttgg cagaacatat ccatcgcgtc    6180
cgccatctcc agcagccgca cgcggcgcat ctcgggcagc gttgggtcct ggccacgggt    6240
gcgcatgatc gtgctcctgt cgttgaggac ccggctaggc tggcggggtt gccttactgg    6300
ttagcagaat gaatcaccga tacgcgagcg aacgtgaagc gactgctgct gcaaaacgtc    6360
tgcgacctga gcaacaacat gaatggtctt cggtttccgt gtttcgtaaa gtctggaaac    6420
gcggaagtca gcgccctgca ccattatgtt ccggatctgc atcgcaggat gctgctggct    6480
accctgtgga acacctacat ctgtattaac gaagcgctgg cattgaccct gagtgatttt    6540
tctctggtcc cgccgcatcc ataccgccag ttgtttaccc tcacaacgtt ccagtaaccg    6600
ggcatgttca tcatcagtaa cccgtatcgt gagcatcctc tctcgtttca tcggtatcat    6660
tacccccatg aacagaaatt ccccctaca cggaggcatc aagtgaccaa acaggaaaaa    6720
accgccctta acatggcccg ctttatcaga agccagacat taacgcttct ggagaaactc    6780
aacgagctgg acgcggatga acaggcagac atctgtgaat cgcttcacga ccacgctgat    6840
gagctttacc gcagctgcct cgcgcgtttc ggtgatgacg gtgaaaacct ctgacacatg    6900 cagctccccgg agacggtcac agcttgtctg taagcggatg ccgggagcag acaagcccgt    6960
cagggcgcgt cagcgggtgt tggcgggtgt cggggcgcag ccatgaccca gtcacgtagc    7020
gatagcggag tgtatactgg cttaactatg cggcatcaga gcagattgta ctgagagtgc    7080
accatatatg cggtgtgaaa taccgcacag atgcgtaagg agaaaatacc gcatcaggcg    7140
ctcttccgct tcctcgctca ctgactcgct gcgctcggtc gttcggctgc ggcgagcggt    7200
atcagctcac tcaaaggcgg taatacggtt atccacagaa tcaggggata acgcaggaaa    7260
gaacatgtga gcaaaaggcc agcaaaaggc caggaaccgt aaaaaggccg cgttgctggc    7320 gttttccat aggctccgcc cccctgacga gcatcacaaa aatcgacgct caagtcagag    7380
gtggcgaaac ccgacaggac tataaagata ccaggcgttt ccccctggaa gctccctcgt    7440
gcgctctcct gttccgaccc tgccgcttac cggatacctg tccgcctttc tcccttcggg    7500
aagcgtggcg ctttctcata gctcacgctg taggtatctc agttcggtgt aggtcgttcg    7560
```

```
ctccaagctg ggctgtgtgc acgaacccccc cgttcagccc gaccgctgcg ccttatccgg    7620
taactatcgt cttgagtcca acccggtaag acacgactta tcgccactgg cagcagccac    7680
tggtaacagg attagcagag cgaggtatgt aggcggtgct acagagttct gaagtggtg    7740 gcctaactac ggctacacta aaggacagt atttggtatc tgcgctctgc tgaagccagt    7800
taccttcgga aaaagagttg gtagctcttg atccggcaaa caaaccaccg ctggtagcgg    7860
tggttttttt gtttgcaagc agcagattac gcgcagaaaa aaaggatctc aagaagatcc    7920
tttgatcttt tctacggggt ctgacgctca gtggaacgaa aactcacgtt aagggatttt    7980
ggtcatgaga ttatcaaaaa ggatcttcac ctagatcctt ttaaattaaa aatgaagttt    8040
taaatcaatc taaagtatat atgagtaaac ttggtctgac agttaccaat gcttaatcag    8100
tgaggcacct atctcagcga tctgtctatt tcgttcatcc atagttgcct gactccccgt    8160
cgtgtagata actacgatac gggagggctt accatctggc cccagtgctg caatgatacc    8220
gcgagaccca cgctcaccgg ctccagattt atcagcaata aaccagccag ccggaagggc    8280
cgagcgcaga agtggtcctg caactttatc cgcctccatc cagtctatta attgttgccg    8340
ggaagctaga gtaagtagtt cgccagttaa tagtttgcgc aacgttgttg ccattgctgc    8400
aggcatcgtg gtgtcacgct cgtcgtttgg tatggcttca ttcagctccg gttcccaacg    8460
atcaaggcga gttacatgat cccccatgtt gtgcaaaaaa gcggttagct ccttcggtcc    8520
tccgatcgtt gtcagaagta agttggccgc agtgttatca ctcatggtta tggcagcact    8580
gcataattct cttactgtca tgccatccgt aagatgcttt tctgtgactg gtgagtactc    8640
aaccaagtca ttctgagaat agtgtatgcg gcgaccgagt tgctcttgcc cggcgtcaac    8700
acgggataat accgcgccac atagcagaac tttaaaagtg ctcatcattg gaaaacgttc    8760
ttcggggcga aaactctcaa ggatcttacc gctgttgaga tccagttcga tgtaacccac    8820
tcgtgcaccc aactgatctt cagcatcttt tactttcacc agcgtttctg gtgagcaaa    8880 aacaggaagg caaaatgccg caaaaaaggg aataagggcg acacggaaat gttgaatact    8940
catactcttc ctttttcaat attattgaag catttatcag ggttattgtc tcatgagcgg    9000
atacatattt gaatgtattt agaaaaataa acaaataggg gttccgcgca catttccccg    9060
aaaagtgcca cctgacgtct aagaaaccat tattatcatg acattaacct ataaaaatag    9120
gcgtatcacg aggccctttc gtcttcaaga att                                 9153

<210> SEQ ID NO 26
<211> LENGTH: 45
<212> TYPE: DNA
<213> ORGANISM: artificial
<220> FEATURE:
<223> OTHER INFORMATION: primer

<400> SEQUENCE: 26
gttctgcagt taaggaggta acatatgaaa accctgctcc aactc              45

<210> SEQ ID NO 27
<211> LENGTH: 36
<212> TYPE: DNA
<213> ORGANISM: artificial
<220> FEATURE:
<223> OTHER INFORMATION: primer

<400> SEQUENCE: 27
gttggatccg tcgaccctac gcaattgctt ttgcgg                        36
```

```
<210> SEQ ID NO 28
<211> LENGTH: 24
<212> TYPE: DNA
<213> ORGANISM: artificial
<220> FEATURE:
<223> OTHER INFORMATION: primer

<400> SEQUENCE: 28
tggaacgaat ttttcgccat tttc                                               24

<210> SEQ ID NO 29
<211> LENGTH: 18
<212> TYPE: DNA
<213> ORGANISM: artificial
<220> FEATURE:
<223> OTHER INFORMATION: primer

<400> SEQUENCE: 29
gaaggtgtct ttctcgcg                                                      18

<210> SEQ ID NO 30
<211> LENGTH: 23
<212> TYPE: DNA
<213> ORGANISM: artificial
<220> FEATURE:
<223> OTHER INFORMATION: primer

<400> SEQUENCE: 30
tgatagggtc ttttaccagc act                                                23

<210> SEQ ID NO 31
<211> LENGTH: 22
<212> TYPE: DNA
<213> ORGANISM: artificial
<220> FEATURE:
<223> OTHER INFORMATION: primer

<400> SEQUENCE: 31
taatggcgtc gagcgtccgg tt                                                 22

<210> SEQ ID NO 32
<211> LENGTH: 24
<212> TYPE: DNA
<213> ORGANISM: artificial
<220> FEATURE:
<223> OTHER INFORMATION: primer

<400> SEQUENCE: 32
cgccagggtt ttcccagtca cgac                                               24
```